United States Patent [19]

Janssens et al.

[11] Patent Number: 5,071,846

[45] Date of Patent: Dec. 10, 1991

[54] ANTI-HISTAMINIC ((BICYCLIC HETEROCYCLYL) METHYL AND -HETERO) SUBSTITUTED HEXAHYDRO-1H-AZEPINES AND PYRROLIDINES

[75] Inventors: Frans E. Janssens, Bonheiden; Gaston S. M. Diels, Ravels; Geert Pille, Edegem, all of Belgium

[73] Assignee: Janssen Pharmaceutica N.V., Beerse, Belgium

[21] Appl. No.: 609,989

[22] Filed: Nov. 6, 1990

Related U.S. Application Data

[60] Division of Ser. No. 338,440, Apr. 13, 1989, Pat. No. 4,988,689, which is a continuation of Ser. No. 198,960, May 26, 1988, abandoned, which is a continuation-in-part of Ser. No. 68,515, Jul. 1, 1987, abandoned.

[51] Int. Cl.$^5$ .................. A61K 31/55; A61K 31/435; C07D 471/04

[52] U.S. Cl. .................. 514/212; 514/253; 514/256; 514/261; 514/262; 514/275; 514/303; 514/338; 540/597; 540/603; 544/238; 544/265; 544/277; 544/297; 544/310; 544/319; 544/333; 544/405; 544/56; 544/61; 544/127; 546/118; 546/271

[58] Field of Search .............. 544/238, 265, 277, 297, 544/310, 319, 333, 405, 56, 61, 127; 540/597, 603; 546/118, 271; 548/181, 327; 514/212, 253, 256, 261, 262, 275, 303, 338

[56] References Cited

PUBLICATIONS

Janssens et al., J. Med. Chem., 28, pp. 1925–1933 (1985).

*Primary Examiner*—Bernard Dentz
*Attorney, Agent, or Firm*—Charles J. Metz

[57] ABSTRACT

[(Bicyclic heterocyclyl)methyl and —hetero] substituted hexahydro—1H—azepines and pyrrolidines and their pharmaceutically acceptable acid addition salts having anti—histaminic properties, compositions containing the same, and methods of treating allergic diseases in warm-blooded animals.

18 Claims, No Drawings

5,071,846

ANTI-HISTAMINIC ((BICYCLIC HETEROCYCLYL) METHYL AND -HETERO) SUBSTITUTED HEXAHYDRO-1H-AZEPINES AND PYRROLIDINES

CROSS-REFERENCE TO RELATED APPLICATIONS

This application is a division of application Ser. No. 338,440, filed Apr. 13, 1989, now U.S. Pat. No. 4,988,689, which was a continuation of application Ser. No. 198,960, filed May 26, 1988, now abandoned, which was a continuation-in-part of application Ser. No. 68,515, filed July 1, 1987, now abandoned.

BACKGROUND OF THE INVENTION

In the U.S. Pat. No. 4,219,559 there are described a number of 1-substituted N-heterocyclyl-4-piperidinamines as compounds having useful anti-histaminic properties.

In the U.S. Pat. Nos. 4,556,660, 4,634,704, 4,695,569 and 4,588,722 there are described further series of N-heterocyclyl-4-piperidinamines as compounds having useful anti-histaminic and serotonin-antagonistic properties.

In the European Patent Application No. 151,826, published Aug. 21, 1985 which corresponds to U.S. Ser. No. 671,135 there are described a number of 4-(bicyclic heterocyclyl)methyl and —heteropiperidines having useful anti-histaminic and serotonin-antagonistic properties whereas in the European Patent Application No. 206,415, published Dec. 30, 1986 which corresponds to U.S. Ser. No. 858,339 there are described some anti-histaminic (4-piperidinylmethyl and —hetero)purines.

The compounds of the present invention differ therefrom by the fact that they contain a pyrrolidine or hexahydro-1H-azepine moiety and by their favourable pharmacological properties.

DESCRIPTION OF THE INVENTION

The invention is concerned with novel substituted benzimidazole derivatives which can structurally be represented by the formula

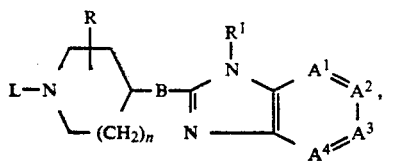

(I)

the pharmaceutically acceptable acid addition salts and the stereochemically isomeric forms thereof, wherein
—$A^1$=$A^2$—$A^3$=$A^4$— is a bivalent radical having the formula

| | |
|---|---|
| —CH=CH—CH=CH—, | (a-1) |
| —N=CH—CH=CH—, | (a-2) |
| —CH=N—CH=CH—, | (a-3) |
| —CH=CH—N=CH—, | (a-4) |
| —CH=CH—CH=N—, | (a-5) |
| —N=CH—N=CH—, or | (a-6) |
| —CH=N—CH=N—, | (a-7) | wherein one or two hydrogen atoms in said radicals (a-1)–(a-7) may, each independently from each other, be replaced by halo, $C_{1-6}$alkyl, $C_{1-6}$alkyloxy, trifluoromethyl or hydroxy;

$R^1$ is hydrogen, $C_{1-10}$alkyl, $C_{3-6}$cycloalkyl, $Ar^1$ or $C_{1-6}$alkyl substituted with one or two $Ar^1$ radicals;

B is $NR^2$, $CH_2$, O, S, SO or $SO_2$; said $R^2$ being hydrogen, $C_{1-6}$alkyl, $C_{3-6}$cycloalkyl, $C_{1-6}$alkylcarbonyl, $C_{1-6}$alkyloxycarbonyl and $Ar^2$—$C_{1-6}$alkyl;

R is hydrogen or $C_{1-6}$alkyl;

n is 0 or 2;

L is hydrogen, $C_{1-6}$alkylcarbonyl, $C_{1-6}$alkylsulfonyl, $C_{1-6}$alkyloxycarbonyl, $Ar^2$—$C_{1-6}$alkyloxycarbonyl, $Ar^2$-carbonyl, $Ar^2$-sulfonyl, $C_{3-6}$cycloalkyl, $C_{2-6}$alkenyl optionally substituted with $Ar^2$, $C_{1-12}$alkyl, a radical of formula

| | |
|---|---|
| -Alk-$R^3$ | (b-1) |
| -Alk-Y—$R^4$ | (b-2) |
| -Alk-$Z^1$—$\overset{\overset{X}{\|\|}}{C}$—$Z^2$—$R^5$, or | (b-3) |
| —$CH_2$—CHOH—$CH_2$—O—$R^6$; | (b-4) | wherein $R^3$ is $Ar^2$, Het, cyano, isocyanato, isothiocyanato, $Ar^2$-sulfonyl or halo;

$R^4$ is hydrogen, $Ar^2$, Het or $C_{1-6}$alkyl optionally substituted with halo, $Ar^2$ or Het;

$R^5$ is hydrogen, $Ar^2$, Het or $C_{1-6}$alkyl optionally substituted with halo, $Ar^2$ or Het;

$R^6$ is $Ar^2$ or naphthalenyl;

Y is O, S, $NR^7$;

said $R^7$ being hydrogen, $C_{1-6}$alkyl, $C_{1-6}$alkylcarbonyl or $Ar^1$-carbonyl;

$Z^1$ and $Z^2$ each independently are O, S, $NR^8$ or a direct bond;

said $R^8$ being hydrogen or $C_{1-6}$alkyl;

X is O, S or $NR^9$;

said $R^9$ is hydrogen, $C_{1-6}$alkyl or cyano;

each Alk independently being $C_{1-6}$alkanediyl;

Het is a five- or six-membered heterocyclic ring containing 1, 2, 3 or 4 heteroatoms, said heteroatoms being selected from the group consisting of oxygen, sulfur and nitrogen, provided that no more than two oxygens or sulfurs are present, said five or six-membered ring being optionally condensed with a five- or six-membered carbocyclic or heterocyclic ring also containing 1, 2, 3 or 4 heteroatoms, the latter heteroatoms being selected from the group consisting of oxygen, sulfur and nitrogen, provided that no more than 2 oxygens or sulfurs are present, and when said Het is a bicyclic ring system it may optionally be substituted with up to 6 substituents, and when said Het is a monocyclic ring system it may optionally be substituted with up to 3 substituents, said substituents of Het being selected from the group consisting of a bivalent radical of formula =X; halo; isocyanato; isothiocyanato; nitro; cyano; trifluoromethyl; a radical of formula —A; a radical of formula —Y—A; or a radical of formula —$Z^1$—C(=X)—$Z^2$—A; wherein said =X independently has the same meaning of the previously defined X and A is hydrogen, $Ar^2$ or $C_{1-6}$alkyl being optionally substituted with $Ar^2$, $C_{1-6}$alkyloxy, $Ar^2$—O, hydroxy, or $C_{1-6}$alkyloxycarbonyl; and Y, $Z^1$ and $Z^2$ independently have the same meaning of the previously defined Y, $Z^1$ and $Z^2$; provided that (i) when in the radical —Y—A, A is hydrogen, then Y is other than a direct bond, or (ii) when in the radical —$Z^1$—C(=X)—$Z^2$—A, A is hydrogen and $Z^1$ is $NR^8$, O or S, then $Z^2$ is other than O or S; preferably the sum of heteroatoms in the above defined Het is less than 6;

$Ar^1$ is a member selected from the group consisting of phenyl, being optionally substituted with 1, 2 or 3 substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl; thienyl; halothienyl; furanyl; $C_{1-6}$alkyl substituted furanyl; pyridinyl; pyrimidinyl; pyrazinyl; thiazolyl and imidazolyl optionally substituted with $C_{1-6}$alkyl; and $Ar^2$ is a member selected from the group consisting of phenyl being optionally substituted with 1, 2 or 3 substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

As used in the foregoing definitions the term halo is generic to fluoro, chloro, bromo and iodo; the term "$C_{1-6}$alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-12}$alkyl" is meant to include $C_{1-6}$alkyl radicals, as defined hereinabove, and the higher homologs thereof having from 7 to 12 carbon atoms; the term "$C_{3-6}$cycloalkyl" is generic to cyclopropyl, cyclobutyl, cyclopentyl and cyclohexyl; the term "$C_{2-6}$alkenyl" defines straight and branch chained hydrocarbon radicals containing one double bond and having from 2 to 6 carbon atoms such as, for example, ethenyl, 2-propenyl, 3-butenyl, 2-butenyl, 2-pentenyl, 3-pentenyl, 3-methyl-2-butenyl and the like; and when a $C_{3-6}$alkenyl is substituted on a heteroatom, then the carbon atom of said $C_{3-6}$alkenyl connected to said heteroatom preferably is saturated.

It is to be understood that the compounds of formula (I) may exist in hydrated or in solvent addition forms and that the invention includes all such forms.

It is evident that in the compounds of formula (I) wherein $R^3$, $R^4$ or $R^5$ is Het, said Het may be unsaturated or partly or completely saturated.

The compounds of formula (I) wherein Het is a heterocycle which is substituted with a hydroxy, mercapto or amino radical may contain in their structure a keto-enol tautomeric system or a vinylog system thereof, and consequently these compounds may be present in their keto form as well as their enol form.

In particularly Het is (i) an optionally substituted five- or six-membered heterocyclic ring containing 1, 2, 3 or 4 heteroatoms selected from the group consisting of oxygen, sulfur and nitrogen, provided that no more than two oxygens or sulfurs are present; or Het is (ii) an optionally substituted five- or six-membered heterocyclic ring containing 1 or 2 heteroatoms selected from the group consisting of oxygen, sulfur and nitrogen, being ortho-condensed with an optionally substituted five- or six-membered ring through two ring carbon atoms or one ring carbon and one ring nitrogen atom, containing in the remainder of the condensed ring only carbon atoms; or Het is (iii) an optionally substituted five- or six-membered heterocyclic ring containing 1 or 2 heteroatoms selected from the group consisting of oxygen, sulfur and nitrogen, being ortho-condensed with an optionally substituted five- or six-membered heterocyclic ring through two ring carbon atoms or one ring carbon and one ring nitrogen atom, containing in the remainder of the condensed ring 1 or 2 heteroatoms selected from the group consisting of oxygen, sulfur and nitrogen; wherein Het may optionally be substituted with up to 2 substituents when Het is a monocyclic ring system, and wherein Het may optionally be substituted with up to 5 substituents when Het is a bicyclic ring system, said substituents being the same as previously described.

In more detail Het is a member selected from the group consisting of pyridinyl which is optionally substituted with one or two substituents each independently selected from halo, amino, mono- and di($C_{1-6}$alkyl)amino, $Ar^2$—$C_{1-6}$alkylamino, nitro, cyano, aminocarbonyl, $C_{1-6}$alkyl, $C_{1-6}$alkyloxy, $C_{1-6}$alkylthio, $C_{1-6}$alkyloxycarbonyl, hydroxy, $C_{1-6}$alkylcarbonyloxy, $Ar^2$—$C_{1-6}$alkyl and carboxyl; pyridinyloxide optionally substituted with nitro; pyrimidinyl which is optionally substituted with one or two substituents each independently selected from the group consisting of halo, amino, hydroxy, $C_{1-6}$alkyl, $C_{1-6}$alkyloxy, $C_{1-6}$alkylthio and $Ar^2$—$C_{1-6}$alkyl; pyridazinyl which is optionally substituted with $C_{1-6}$alkyl or halo; pyrazinyl which is optionally substituted with halo, amino or $C_{1-6}$alkyl; thienyl which is optionally substituted with halo or $C_{1-6}$alkyl; furanyl which is optionally substituted with halo or $C_{1-6}$alkyl; pyrrolyl which is optionally substituted with $C_{1-6}$alkyl; thiazolyl which is optionally substituted with $C_{1-6}$alkyl, $C_{1-6}$alkyloxycarbonyl, $Ar^2$ or $Ar^2$—$C_{1-6}$alkyl; imidazolyl which is optionally substituted with one or two substituents each independently selected from $C_{1-6}$alkyl and nitro; tetrazolyl which is optionally substituted with $C_{1-6}$alkyl; 1,3,4-thiadiazolyl which is optionally substituted with $C_{1-6}$alkyl; 5,6-dihydro-4H-1,3-thiazin-2-yl which is optionally substituted with $C_{1-6}$alkyl; 4,5-dihydrothiazolyl which is optionally substituted with $C_{1-6}$alkyl; oxazolyl which is optionally substituted with $C_{1-6}$alkyl; 4,5-dihydro-5-oxo-1H-tetrazolyl which is optionally substituted with $C_{1-6}$alkyl; 1,4-dihydro-2,4-dioxo-3(2H)-pyrimidinyl being optionally substituted with $C_{1-6}$alkyl; 4,5-dihydro-4-oxo-2-pyrimidinyl; 2-oxo-3-oxazolidinyl; indolyl which is optionally substituted with $C_{1-6}$alkyl; quinolinyl which is optionally substituted with hydroxy or $C_{1-6}$alkyl; quinazolinyl which is optionally substituted with hydroxy or $C_{1-6}$alkyl; quinoxalinyl which is optionally substituted with $C_{1-6}$alkyl; phthalazinyl which is optionally substituted with halo; 1,3-dioxo-1H-isoindol-2(3H)-yl; 2,3-dihydro-3-oxo-4H-benzoxazinyl and 2,3-dihydro-1,4-benzodioxinyl, both being optionally substituted with $C_{1-6}$alkyl or halo; dioxanyl being optionally substituted with $C_{1-6}$alkyl; 2-oxo-2H-1-benzopyranyl and 4-oxo-4H-1-benzopyranyl both being optionally substituted with $C_{1-6}$alkyl; morfolinyl; thiomorfolinyl; piperidinyl; and a radical of formula

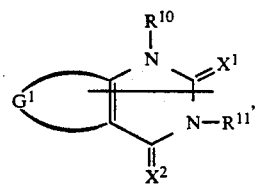 (c-1)

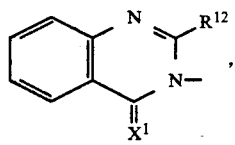 (c-2)

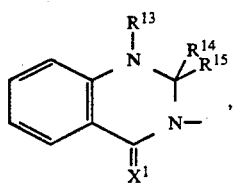 (c-3)

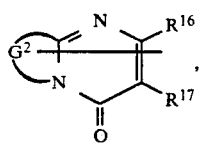 (c-4)

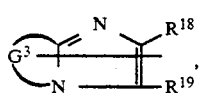 (c-5)

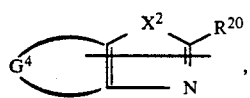 (c-6)

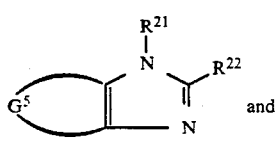 (c-7) and

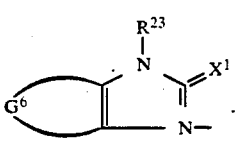 (c-8)

wherein
$X^1$ and $X^2$ are each independently O or S;
$R^{10}$, $R^{11}$, $R^{13}$, $R^{21}$ and $R^{23}$ are each independently hydrogen, $C_{1-6}$alkyl, $Ar^2$—$C_{1-6}$alkyl, hydroxy$C_{1-6}$alkyl or $C_{1-6}$alkyloxycarbonyl;
$R^{12}$, $R^{14}$, $R^{15}$, $R^{16}$, $R^{17}$, $R^{18}$, $R^{19}$, $R^{20}$ and $R^{22}$ are each independently hydrogen, $C_{1-6}$alkyl, hydroxy, mercapto, $C_{1-6}$alkyloxy, $C_{1-6}$alkylthio, halo and ($C_{1-6}$alkyloxycarbonyl)$C_{1-6}$alkyl;
$G^1$ is —CH=CH—CH=CH—, —S—CH=CH— or —N=CH—NH—;
$G^2$ is —CH=CH—CH=CH—, —S—(CH$_2$)$_2$—, —S—(CH$_2$)$_3$—, —(CH$_2$)$_4$— or —S—CH=CH—;
$G^3$ is —CH=CH—CH=CH—, —CH$_2$—N-H—(CH$_2$)$_2$—, —S—CH=CH—, —S—(CH$_2$)$_3$—, —N=CH—CH=CH—, —CH=N—CH=CH—, —CH=CH—N=CH—, —CH=CH—CH=N—, —N=CH—N=CH— or —CH=N—CH=N—;
$G^4$ is —CH=CH—CH=CH—, —CH$_2$—N-H—(CH$_2$)$_2$—, —N=CH—CH=CH—, —CH=N—CH=CH—, —CH=CH—N=CH—, —CH=CH—CH=N—, —N=CH—N=CH— or —CH=N—CH=N—;
$G^5$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—;
$G^6$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—;

wherein one or two hydrogen atoms in said radicals $G^1$, $G^2$, $G^3$, $G^4$, $G^5$ or $G^6$ or in the benzene part of the radicals of formula (c-2) or (c-3) may be replaced by $C_{1-6}$alkyl, $C_{1-6}$alkylthio, $C_{1-6}$alkyloxy or halo where said hydrogen atom is bonded on a carbon atom, or by $C_{1-6}$alkyl, $C_{1-6}$alkylcarbonyl, $Ar^2$—$C_{1-6}$alkyl, where said hydrogen is bonded on a nitrogen atom;

An interesting group among the compounds of formula (I) comprises those compounds of formula (I) wherein n=2.

Another interesting group among the compounds of formula (I) comprises those compounds of formula (I) wherein n=0.

Among the above groups those compounds of formula (I) are preferred wherein Het is the particular Het described hereinabove.

More particularly preferred compounds are those particularly preferred compounds wherein R is hydrogen, $R^1$ is $C_{1-6}$alkyl substituted with one $Ar^1$ and B is NH or CH$_2$.

Especially preferred compounds are those more particularly preferred compounds wherein L is hydrogen, $C_{1-6}$alkyl or a radical of formula (b-1), (b-2) or (b-3) and B is NH.

More especially preferred compounds within the invention are those especially preferred compounds wherein $R^3$, $R^4$ and $R^5$ are each $Ar^2$ or Het, $R^7$ is hydrogen or $C_{1-6}$alkyl, X is O, and $Z^1$ and $Z^2$ are each independently NH or a direct bond.

A particular subgroup of compounds of formula (I) comprises those compounds, preferred, particularly preferred, more particularly preferred, especially preferred and more especially preferred compounds wherein $A^1=A^2-A^3=A^4$ is a bivalent radical having the formula (a-1).

Another particular subgroup of compounds of formula (I) comprises those compounds, preferred, particularly preferred, more particularly preferred, especially preferred and more especially preferred compounds wherein $A^1=A^2-A^3=A^4$ is a bivalent radical having a formula (a-2) through (a-7), with (a-2) being the most interesting group.

The compounds of formula (I) can generally be prepared by reacting an intermediate of formula (II) with a diamine of formula (III).

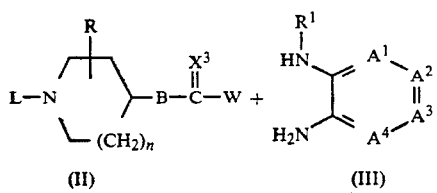 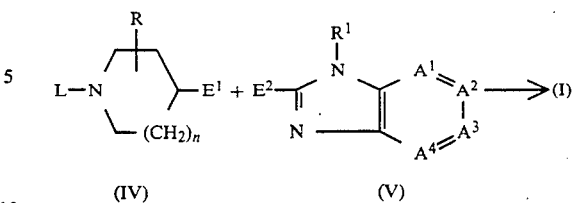

In some instances the reaction of (II) with (III) first yields an intermediate of formula (II-a)

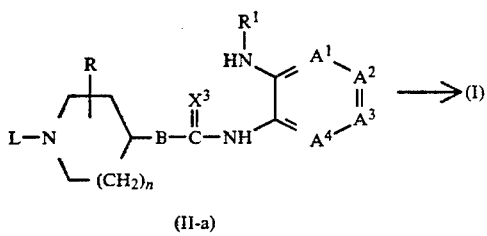

which may in situ or, if desired, after isolation and purifying it, be cyclized to obtain the desired compounds of formula (I).

In the reaction of (II) with (III) and in the following reaction schemes $W^1$ and W represent an appropriate leaving group such as, for example, halo, e.g. chloro, bromo or iodo, or a sulfonyloxy group, e.g. methylsulfonyloxy or 4-methylphenylsulfonyloxy, whereas W may also be alkyloxy, alkylthio, $Ar^2$—O— or $Ar^2$—S—. In (II) and (II-a) $X^3$ denotes O, S or NH.

The pyrrolidine or hexahydro-1H-azepine derivatives of formula (II) may in situ be generated, for example, by converting a pyrrolidine or hexahydro-1H-azepine which is substituted with a —B—C(=$X^3$)—OH radical into an intermediate of formula (II) by reacting the former with thionyl chloride, phosphor trichloride, phosphoryl chloride, polyphosphoric acid, phosphoroxy chloride and the like.

The reaction of (II) with (III) may be conducted in a suitable solvent such as, for example, a hydrocarbon, e.g., benzene, hexane; an ether, e.g., 1,1'-oxybisethane, tetrahydrofuran; a ketone, e.g., 2-propane, 2-butanone; an alcohol, e.g., methanol, ethanol, 2-propanol, 1-butanol; a halogenated hydrocarbon, e.g., trichloromethane, dichloromethane, an organic acid, e.g., acetic acid, propanoic acid; a polar aprotic solvent e.g., N,N-dimethylformamide, N,N-dimethylacetamide and the like; and mixtures of such solvents. Depending upon the solvent and nature of W it may be appropriate to add a suitable base and/or a iodide salt, preferably an alkali metal iodide, to the reaction mixture. Elevated temperatures may enhance the reaction rate.

The compounds of formula (I) can also be prepared by reacting an intermediate of formula (V) with an intermediate of formula (IV) wherein $E^1$ and $E^2$ are selected so that during the reaction a radical —B— is formed.

For example, the compounds of formula (I) can be prepared by reacting an intermediate of formula (IV) wherein $E^1$ is a radical of formula —B—M with an intermediate of formula (V) wherein $E^2$ is a radical of formula —W.

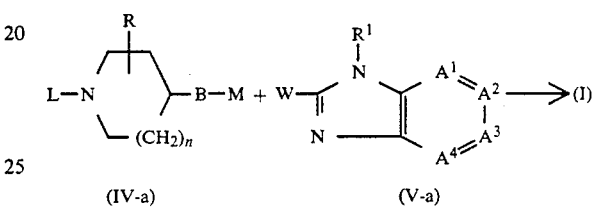

In (IV-a) M is, depending upon the nature of B, hydrogen or an appropriate alkalimetal or earth alkaline metal and in (V-a) W has the previously described meanings. Additionally, the compounds of formula (I) can also be prepared by reacting an intermediate of formula (IV) wherein $E^1$ is $W^1$ with an intermediate of formula (V) wherein $E^2$ is a radical of formula —B—M, said $W^1$ and M having the previously described meanings.

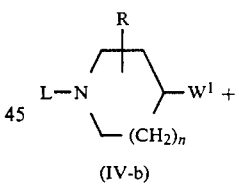

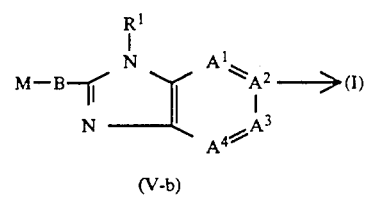

More particularly, the compounds of formula (I) wherein B is —$CH_2$— can also be prepared by reacting an intermediate of formula (IV) wherein $E^1$ represents a radical of formula —$CH_2$—$W^1$, (IV-c), with an intermediate of formula (V) wherein $E^2$ represents M, (V-c) or alternatively, by reacting an intermediate of formula (IV), wherein $E^1$ is a radical of formula —M, (IV-d), with an intermediate of formula (V) wherein $E^2$ is a radical of formula —$CH_2$—$W^1$, (V-d).

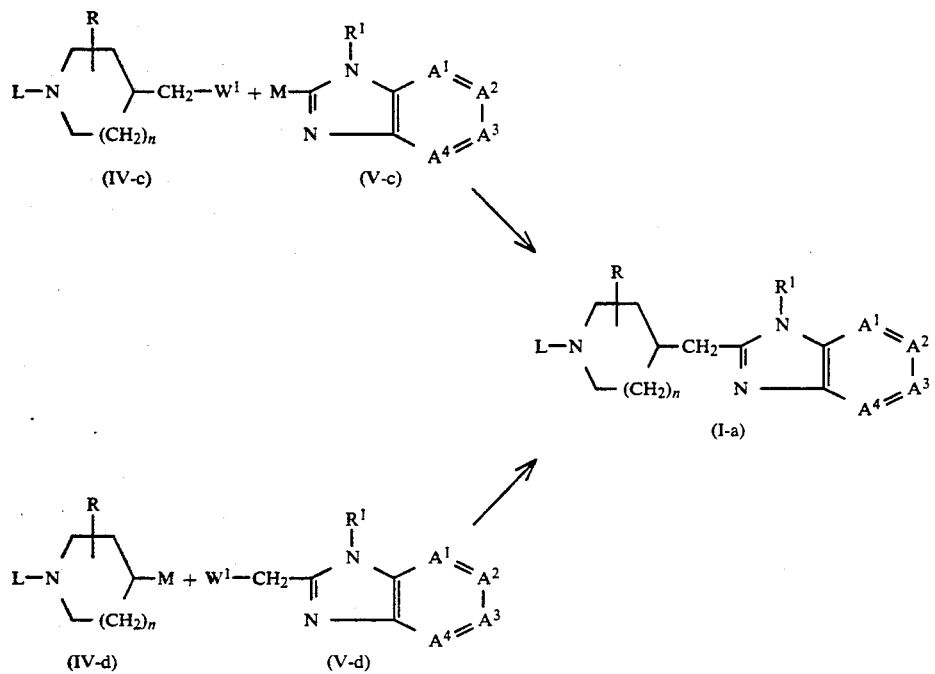

The reactions of (IV-a) with (V-a), (IV-b) with (V-b), (IV-c) with (V-c) and (IV-d) with (V-d) may conveniently be conducted in an appropriate solvent such as for example, an aromatic hydrocarbon, e.g., benzene, methylbenzene; an ether, e.g. 1,4-dioxane, 1,1'-oxybisethane, tetrahydrofuran and the like; a halogenated hydrocarbon, e.g. trichloromethane and the like; N,N-dimethylformamide; N,N-dimethylacetamide; nitrobenzene; dimethyl sulfoxide; 1-methyl-2-pyrrolidinone; and where M is hydrogen, said solvent may also be a $C_{1-6}$alkanol, e.g., methanol, ethanol, 1-butanol and the like; a ketone, e.g., 2-propanone, 4-methyl-2-pentanone and the like. In some instances, the addition of an appropriate base such as, for example, an alkali metal carbonate or hydrogen carbonate, sodium hydride or an organic base such as, for example, N,N-diethylethanamine or N-(1-methylethyl)-2-propanamine and/or the addition of a iodide salt, preferably an alkali metal iodide, may be appropriate. Somewhat elevated temperatures may enhance the rate of the reaction.

Or, the compounds of formula (I) wherein B is —NR²— can also be prepared by reacting an intermediate of formula (IV) wherein E¹ is an oxo radical, (IV-e), with an intermediate of formula (V) wherein E² represents a radical —NHR², (V-e).

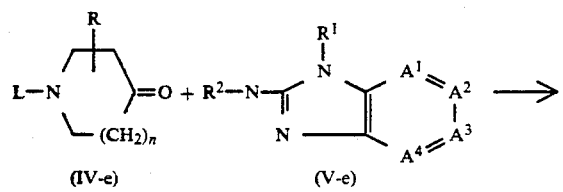

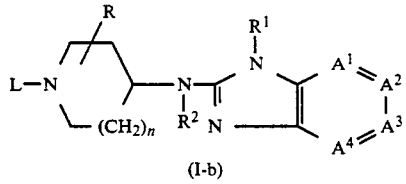

The reaction of (IV-e) with (V-e) is conveniently carried out by treating a mixture of the reactants in a suitable reaction-inert organic solvent with an appropriate reductant. Preferably, the 3-pyrrolidinone or hexahydro-1H-azepine-4-one of formula (IV-e) is first reacted with the benzimidazolamine of formula (V-e) to form an enamine, which optionally may be isolated and further purified, and subsequently subjecting the said enamine to a reduction reaction. Suitable solvents are, for example, water; $C_{1-6}$alkanols, e.g. methanol, ethanol, 2-propanol and the like; cyclic ethers, e.g. 1,4-dioxane and the like; halogenated hydrocarbons, e.g. trichloromethane and the like; N,N-dimethylformamide; N,N-dimethylacetamide; dimethyl sulfoxide and the like; or a mixture of such solvents. Appropriate reductants are for example, metal or complex metal hydrides, e.g. sodium borohydride, lithium aluminiumhydride; or hydrogen, the latter being preferably used in the presence of a suitable catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiopene and the like.

The compounds of formula (I) wherein B is —NH— can also be prepared by a cyclodesulfurization reaction of an appropriate thiourea derivative of formula (VII), which may in situ be formed by condensing an isothiocyanate of formula (VI) with a diamine of formula (III).

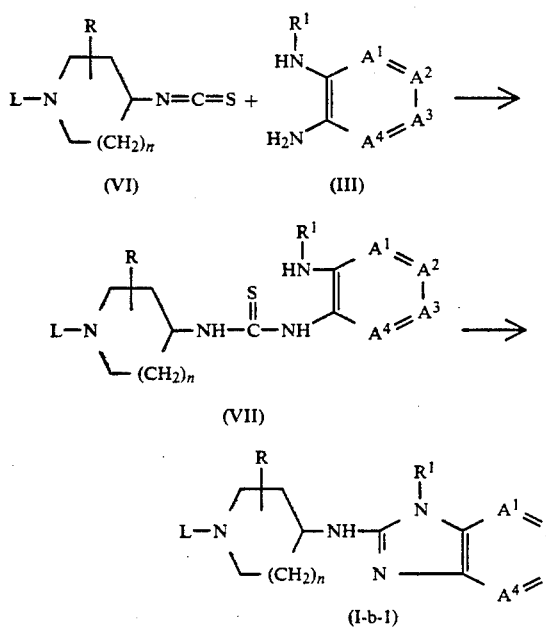

(VI)  (III)

(VII)

(I-b-1)

Said cyclodesulfurization reaction may be carried out by the reaction of (VII) with an appropriate alkyl halide, preferably iodomethane in a suitable reaction-inert organic solvent, e.g., a $C_{1-6}$alkanol such as, methanol, ethanol, 2-propanol and the like. Otherwise, the cyclodesulfurization reaction may be carried out by the reaction of (VII) with an appropriate metal oxide or salt in an appropriate solvent according to art-known procedures. For example, the compounds of formula (I-b-1) can easily be prepared by the reaction of (VII) with a Hg(II) or Pb(II) oxide or salt such as, for example, HgO, $HgCl_2$, $Hg(OAc)_2$, PbO or $Pb(OAc)_2$. In certain instances it may be appropriate to supplement the reaction mixture with a small amount of sulfur. Even so methanediimines, especially dicyclohexylcarbodiimide may be used as cyclodesulfurizing agents.

The compounds of formula (I) can also be prepared by N-alkylating an intermediate of formula (VIII) with an appropriate reagent of formula (IX).

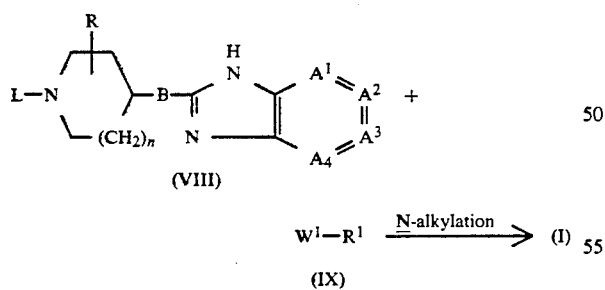

(VIII)

$W^1—R^1$  $\xrightarrow{\text{N-alkylation}}$ (I)

(IX)

The N-alkylation reaction is conveniently conducted in an inert organic solvent such as, for example, an aromatic hydrocarbon, e.g., benzene, methylbenzene, dimethylbenzene, and the like; an alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a polar aprotic solvent, e.g., N,N-dimethylformamide, N,N-dimethylacetamide, dimethyl sulfoxide, nitrobenzene, 1-methyl-2-pyrrolidinone, and the like. The addition of an appropriate base such as, for example, an alkali or an earth alkaline metal carbonate, hydrogen carbonate, hydroxide, and oxide, e.g., sodium carbonate, sodium hydrogen carbonate, potassium carbonate, sodium hydroxide, calcium carbonate, calcium hydroxide, calcium oxide and the like, or an organic base, such as, for example, a tertiary amine, e.g., N,N-diethylethanamine, N-(1-methylethyl)-2-propanamine, 4-ethylmorpholine and the like may be utilized to pick up the acid which is liberated during the course of the reaction. In some instances the addition of a iodide salt, preferably an alkali metal iodide, is appropriate. Somewhat elevated temperatures may enhance the rate of the reaction.

The compounds of formula (I) can also be converted into each other. Some examples of such conversions will be described hereinafter.

In order to simplify the structural representations of the compounds of formula (I) and of certain precursors and intermediates thereof the

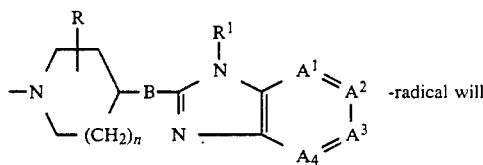 -radical will hereafter be represented by the symbol D.

The compounds of formula (I) wherein L is other then hydrogen, said L being represented by $L^1$, and said compounds being represented by formula (I-c) can generally be prepared by N-alkylating a compound of formula (I) wherein L is hydrogen, said compounds being represented by formula (I-d), with a reagent of formula (X).

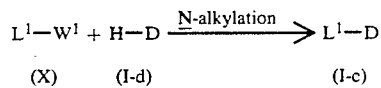

(X)  (I-d)  (I-c)

The said N-alkylation is conveniently carried out according to art-known N-alkylation procedures described hereinabove for the preparation of (I) starting from (VIII) and (IX).

The compounds of formula (I) wherein L is $C_{3-6}$cycloalkyl, $C_{1-12}$alkyl, a radical of formula (b-1), (b-2) or (b-3) said radical L being represented by the radical $L^2H—$, and said compounds being represented by formula (I-c-1) can also be prepared by the reductive N-alkylation reaction of (I-d) with an appropriate ketone or aldehyde of formula $L^2=O$ (XI), said $L^2=O$ being an intermediate of formula $L^2H_2$ wherein two geminal hydrogen atoms are replaced by =O, and $L^2=$ is a geminal bivalent radical comprising $C_{3-6}$cycloalkylidene, $C_{1-12}$alkylidene, $R^3—C_{1-6}$alkylidene, $R^4—Y—C_{1-6}$alkylidene and $R^5—Z^2—C(=X)—Z^1—C_{1-6}$alkylidene.

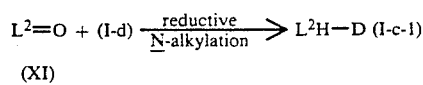

(XI)

Said reductive N-alkylation reaction may conveniently be carried out by catalytically hydrogenating a stirred and heated mixture of the reactants in a suitable reaction inert organic solvent according to art-known catalytic hydrogenating procedures. Suitable solvents are, for example, water; alkanols, e.g., methanol, ethanol, 2-propanol and the like; cyclic ethers, e.g., 1,4-dioxane and the like; halogenated hydrocarbons, e.g., trichloromethane and the like; N,N-dimethylformamide; dimethyl sulfoxide and the like; or a mixture of two or more of such solvents. The term "art-known catalytic hydrogenating procedures" means that the reaction is carried out under hydrogen atmosphere in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I) wherein L is a radical of formula (b-2) wherein $R^4$ is $Ar^2$ or Het, said $R^4$ being represented by $R^{4-a}$ and said compounds by formula (I-c-2) may also be prepared by alkylating a compound of formula (I) wherein L is a radical of formula (b-2) wherein $R^4$ is hydrogen, said compounds being represented by formula (I-c-3), with a reagent of formula (XII).

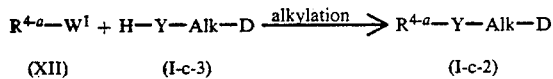

$$R^{4-a}-W^1 + H-Y-Alk-D \xrightarrow{\text{alkylation}} R^{4-a}-Y-Alk-D$$

(XII)　　　(I-c-3)　　　　　　　(I-c-2)

The compounds of formula (I-c-2) can also be prepared by alkylating a compound of formula (I-c-4) with a reagent of formula (XIII).

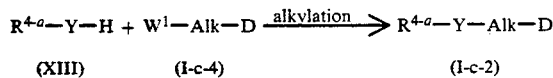

$$R^{4-a}-Y-H + W^1-Alk-D \xrightarrow{\text{alkylation}} R^{4-a}-Y-Alk-D$$

(XIII)　　　(I-c-4)　　　　　　　(I-c-2)

The alkylation reactions of (XII) with (I-c-3) and (XIII) with (I-c-4) may conveniently be conducted in an inert organic solvent such as, for example, an aromatic hydrocarbon, e.g., benzene, methylbenzene, dimethylbenzene; a ketone, e.g., 2-propanone, 4-methyl-2-pentanone; an ether, e.g., 1,4-dioxane, 1,1'-oxybisethane, tetrahydrofuran; and a polar aprotic solvent, e.g., N,N-dimethylformamide; N,N-dimethylacetamide; dimethyl sulfoxide; nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. Somewhat elevated temperatures may enhance the rate of the reaction.

The compounds of formula (I) wherein L is a radical of formula (b-3) wherein $Z^1$ is NH and $Z^2$ is other than a direct bond, said $Z^2$ being represented by $Z^{2-a}$, and said compounds by (I-c-5) can be prepared by reacting an isocyanate or isothiocyanate of formula (I-c-6) with a reagent of formula (XIV).

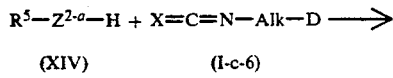

$$R^5-Z^{2-a}-H + X=C=N-Alk-D \longrightarrow$$

(XIV)　　　(I-c-6)

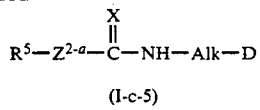

$$R^5-Z^{2-a}-\overset{\overset{X}{\|}}{C}-NH-Alk-D$$

(I-c-5)

The compounds of formula (I) wherein L is a radical of formula (b-3) wherein $Z^2$ is NH and $Z^1$ is other than a direct bond, said $Z^1$ being represented by $Z^{1-a}$ and said compounds by (I-c-7), can be prepared by reacting a isocyanate or isothiocyanate of formula (XV) with a compound of formula (I-c-8).

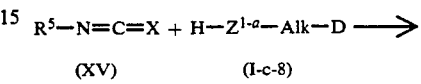

$$R^5-N=C=X + H-Z^{1-a}-Alk-D \longrightarrow$$

(XV)　　　　　(I-c-8)

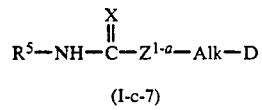

$$R^5-NH-\overset{\overset{X}{\|}}{C}-Z^{1-a}-Alk-D$$

(I-c-7)

The reaction of (XIV) with (I-c-6), or (XV) with (I-c-8) is generally conducted in a suitable reaction-inert solvent such as, for example, an ether, e.g., tetrahydrofuran and the like. Elevated temperatures may be suitable to enhance the rate of the reaction.

The compounds of formula (I) wherein L is a radical of formula (b-3) wherein $Z^2$ is a direct bond and $Z^1$ is other than a direct bond, said compounds being represented by (I-c-9), can be prepared by reacting a reagent of formula (XVI) or a functional derivative thereof with a compound of formula (I-c-8).

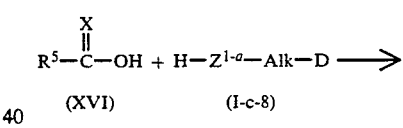

$$R^5-\overset{\overset{X}{\|}}{C}-OH + H-Z^{1-a}-Alk-D \longrightarrow$$

(XVI)　　　　　(I-c-8)

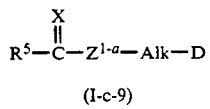

$$R^5-\overset{\overset{X}{\|}}{C}-Z^{1-a}-Alk-D$$

(I-c-9)

The reaction of (XVI) with (I-c-8) may generally be conducted following art-known esterification- or amidation reaction procedures. For example, the carboxylic acid may be converted into a reactive derivative, e.g., an anhydride or a carboxylic acid halide, which subsequently, is reacted with (I-c-8); or by reacting (XVI) and (I-c-8) with a suitable reagent capable of forming amides or esters, e.g., N,N-methanetetraylbis[cyclohexamine], 2-chloro-1-methylpyridinium iodide and the like. Said reactions are most conveniently conducted in a suitable solvent such as, for example, an ether, e.g., tetrahydrofuran, a halogenated hydrocarbon, e.g., dichloromethane, trichloromethane or a polar aprotic solvent. The addition of a base such as, N,N-diethylethanamine may be appropriate.

The compounds of formula (I) wherein L is a radical of formula $L^3$—$C_{2-6}$alkanediyl, said $L^3$ being $Ar^2$, Het, $Ar^2$-sulfonyl or a radical of formula $R^5$—$Z^2$—C(=X)—, and said compounds being represented by formula (I-c-10), may also be prepared by reacting an appropriate alkenylene of formula (XVII) with a compound of formula (I-d).

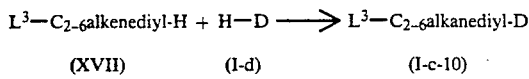

(XVII)   (I-d)   (I-c-10)

The compounds of formula (I) wherein L is a radical of formula (b-4) or a 2-hydroxyethyl, said compounds being represented by formula (I-c-11), may also be prepared by reacting a reagent (XVIII) with a compound of formula (I-d).

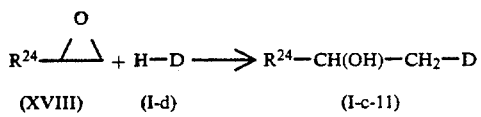

(XVIII)   (I-d)   (I-c-11)

$R^{24}$ in (XVIII) and (I-c-11) being hydrogen or a radical $R^6$—O—$CH_2$—. The reactions of (XVII) with (I-d) and (XVIII) with (I-d) may be conducted by stirring and, if desired, heating the reactants. The said reactions may be conducted in a suitable solvent such as, for example, a ketone, e.g., 2-propanone, 4-methyl-2-pentanone, an ether, e.g., tetrahydrofuran, 1,1'-oxybisethane, an alcohol, e.g., methanol, ethanol, 1-butanol, a polar aprotic solvent, e.g., N,N-dimethylformamide, N,N-dimethylacetamide, and the like.

The compounds of formula (I) wherein $R^3$, $R^4$ or $R^5$ are Het, may also be prepared following procedures for preparing ring systems which are known in the art or analogues procedures thereof. A number of such cyclization procedures are described in for example, the Published European Patent Publication No. 151,826, incorporated herein by reference. For example, compounds of formula (I-c-12) can be obtained by a cyclodesulfurization reaction of (I-c-13) following similar procedures as described for the preparation of (I-b-1) from (VII).

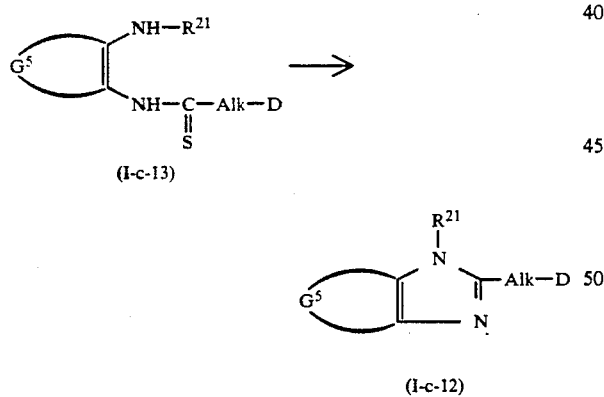

In (I-c-13) and (I-c-12) $G^5$ and $R^{21}$ have the same meanings as described hereinbefore.

The compounds of formula (I) can also be converted into each other following art-known procedures of functional grouptransformation. Some examples of such procedures will be cited hereinafter.

The compounds of formula (I), wherein —B— is —S— may be converted into the corresponding compounds of formula (I), wherein —B— is —SO— or —$SO_2$— by an appropriate oxidation reaction, e.g., by reacting the former compounds with a suitable oxidating agent such as, for example, potassium periodate, a peroxide, e.g., 3-chlorobenzenecarboperoxoic acid, hydrogen peroxide, and the like, in a suitable solvent such as, for example, an ether, e.g., tetrahydrofuran, 1,1'-oxybisethane, a hydrocarbon, e.g., benzene, a halogenated hydrocarbon, e.g., dichloromethane, trichloromethane and the like. In the instance where a sulfinyl is desired, said oxidation reaction is preferably conducted at lower temperatures with approximately one equivalent of the oxidating agent, while where a sulfonyl is desired, said oxidation reaction may be conducted at room or at an elevated temperature with an excess of oxidating agent.

The compounds of formula (I) containing a cyano substituent can be converted into the corresponding amines by stirring and, if desired, heating the starting cyano compounds in a hydrogen containing medium in the presence of a suitable amount of an appropriate catalyst such as, for example, platinum-on-charcoal, Raney-nickel and the like catalyst. Suitable solvents are, for example, methanol, ethanol and the like.

The hydrogen atoms of the amino function(s) of compounds of formula (I) may be substituted following art-known procedures such as, for example, N-alkylation, N-acylation, reductive N-alkylation and the like methods. For example alkylcarbonyl, arylcarbonyl and the like groups may be introduced by reacting the starting amine with an appropriate carboxylic acid or a derivative thereof such as, for example, an acid halide, acid anhydride and the like.

The compounds of formula (I) containing a substituted amine may be converted into the corresponding compounds of formula (I) wherein said nitrogen bears a hydrogen atom following art-known methods for preparing NH group. For example, where said amine is substituted with a $C_{1-6}$alkyloxycarbonyl group by treating the starting material with an acid or a base in a suitable solvent. As suitable acids there may be cited hydrohalic acids, e.g., hydrochloric acid or hydrobromic acid, sulfuric, phosphoric and the like acids preferably employed as an aqueous solution or mixed with, e.g., acetic acid. Suitable bases are the alkali metal hydroxides, hydrides or alkoxides in an aqueous or alcoholic medium. Or, where said nitrogen is substituted with an $Ar^2$—$CH_2$ group, by treating the starting compounds with hydrogen in the presence of a suitable catalyst, e.g., palladium-on-charcoal, platinum-on-charcoal, preferably in an alcoholic medium.

The compounds of formula (I) containing a nitrogen atom substituted with $Ar^2$—$CH_2$— may also be converted into the corresponding compounds where said nitrogen is substituted with $C_{1-6}$alkyloxycarbonyl, for example by treating the former compounds with a $C_{1-6}$alkylcarbonohalidate, e.g., ethyl carbonochloridate in the presence of a suitable solvent, e.g., methylbenzene and, if desired, in the presence of an appropriate base.

The compounds of formula (I) wherein the pyrrolidine or hexahydro-1H-azepine nitrogen is substituted with a $C_{1-6}$alkyloxycarbonyl group may be converted into the corresponding compounds wherein the ring nitrogen is substituted with methyl by reducing the starting compounds with an appropriate reductant such as, lithium tetrahydroaluminate.

The compounds of formula (I) containing an amino group may be converted into the corresponding isothiocyanato containing compounds by treating the starting amino compounds with $CS_2$ optionally in the presence of N,N-methanetetraylbis[cyclohexamine].

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g., hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may also be converted to their therapeutically active non-toxic metal or amine substitution salt forms by treatment with appropriate organic or inorganic bases.

Some intermediates and starting materials in the foregoing preparations are known compounds which may be prepared according to art-known methodologies of preparing said or similar compounds and others are new. A number of such preparation methods will be described hereinafter in more detail.

The intermediates of formula (II), wherein B is CH$_2$, X$^3$ is NH and W is C$_{1-6}$alkyloxy, said intermediates being represented by the formula (II-b), can be prepared by reacting a (cyanomethyl)derivative of formula (XIX) with an alcohol, e.g., methanol, ethanol and the like, in the presence of an acid, e.g., hydrochloric acid.

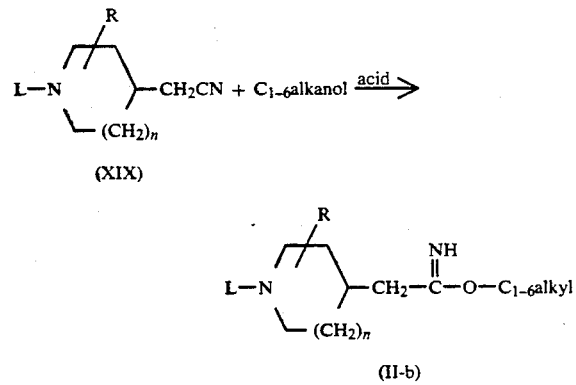

The intermediates of formula (IV) may be prepared by reduction of an appropriate 3-pyrrolidinone or hexahydro-1H-azepin-4-one, if desired, followed by an appropriate art-known groupstransformation procedure, for example, in the instance where a compound of formula (IV-b) is desired, by reacting the thus obtained alcohol with thionyl chloride, methylsulfonyl chloride and the like in order to obtain an appropriate leaving group.

Starting materials such as intermediates of formulae (VI), (VIII), (X) and (XI) can conveniently be prepared following similar procedures as described in, for example, U.S. Pat. Nos. 4,219,559; 4,335,127; 4,342,870; 4,443,451; 4,634,704; 4,695,569 and 4,588,722, which are incorporated herein by reference.

From formula (I) it is evident that the compounds of this invention may have several asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, (1966).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

The compounds of formula (I), the pharmaceutically acceptable acid addition salts and possible stereochemically isomeric forms thereof possess useful pharmacological properties. More particularly, they are active as anti-histaminics which activity can clearly be demonstrated by, e.g., the results obtained in the "Protection of Rats from Compound 48/80-induced lethality"-test, the "Histamine antagonism in Guinea Pig"-test and the "Ascaris Allergy test in Dogs"-test described in Arch. Int. Pharmacodyn. Ther. 251, 39–51 (1981). Apart from their anti-histaminic properties some of the subject compounds also show serotonin-antagonism.

Furthermore the compounds of formula (I), the pharmaceutically acceptable acid addition salts and stereochemically isomeric forms thereof are particularly attractive due to their favourable pharmacokinetical profile. In particularly, some show a rapid onset so that their anti-histaminic effects are almost instantaneously present. Especially those compounds of formula (I) wherein n=2 show an interesting farmacokinetical profile due to their combined rapid onset and favourable limited duration of action.

In view of their anti-histaminic properties, the compounds of formula (I) and their acid addition salts are very useful in the treatment of allergic diseases such as, for example, allergic rhinitis, allergic conjunctivities, chronic urticaria, allergic astma and the like.

In view of their useful pharmacological properties the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention is also related with a method of treating allergic diseases in warm-blooded animals suffering from said allergic diseases by administering an effective anti-allergic amount of a compound of formula (I) or a pharmaceutically acceptable acid addition salt thereof.

Those of skill in treating allergic diseases in warm-blooded animals could easily determine the effective amount from the test results presented hereinafter. In general it is contemplated that an effective amount would be from 0.001 mg/kg to 100 mg/kg body weight, and more preferably from 0.01 mg/kg to 1 mg/kg body weight.

The following examples are intented to illustrate and not to limit the scope of the present invention in all its aspects. Unless otherwise stated all parts therein are by weight.

EXPERIMENTAL PART

A. Preparation of Intermediates

Example 1 a) A mixture of 180.0 parts of 2-chloro-3-nitropyridine, 122.0 parts of 2-thiophenemethanamine, 191.0 parts of sodium carbonate, 1 part of potassium iodide and 810 parts of N,N-dimethylacetamide was stirred for 1.50 hour at 100° C. The reaction mixture was poured into a lot of water (about 4000 parts). The whole was stirred overnight at room temperature. The precipitated product was filtered off and dried in vacuo at 40° C., yielding 251.5 parts of 3-nitro-N-(2-thienylmethyl)-2-pyridinamine; mp. 100° C. (interm. 1).

A mixture of 125 parts of 3-nitro-N-(2-thienylmethyl)-2-pyridinamine and 560 parts of methanol, saturated with ammonia was hydrogenated at normal pressure and at room temperature with 10 parts of platinum-on-charcoal catalyst 5%. After the calculated amount of hydrogen was taken up, the catalyst was filtered off and the filtrate was evaporated. The residue was stirred overnight in 1,1'-oxybisethane. The product was filtered off and dried in vacuo at 40° C., yielding 77 parts (70.8%) of $N^2$-(2-thienylmethyl)-2,3-pyridinediamine; mp. 92.1° C. (interm. 2).

In a similar manner there were also prepared: $N^2$-(2-furanylmethyl)-2,3-pyridinediamine as a residue (interm. 3); $N^1$-[(5-methyl-2-furanyl)methyl]-1,2-benzenediamine as a residue (interm. 4); and $N^2$-[(5-methyl-2-furanyl)methyl]-2,3-pyridinediamine as a residue (interm. 5).

Example 2 a-1) To a stirred mixture of 25 parts of carbonothioic dichloride, 65 parts of water and 210 parts of trichloromethane were added dropwise 9.3 parts of ethyl 3-aminopyrrolidinecarboxylate. Upon completion, the reaction mixture was stirred for 15 minutes at room temperature. 10.7 Parts of calcium carbonate were added portionwise during a period of 10 minutes and stirring was continued overnight at room temperature. The reaction mixture was filtered and the separated organic layer was dried, filtered and evaporated. The residue was purified by column chromatography over silica gel using trichloromethane as eluent. The pure fractions were collected and the eluent was evaporated. The residue was distilled at 6.65 Pa, yielding 7.5 parts (69.3%) of ethyl 3-isothiocyanato-1-pyrrolidinecarboxylate; bp. 101° C. (interm 6).

a-2) To 192 parts of cooled water were added portionwise 12.8 parts of sodium hydroxide. Upon complete addition, 25.3 parts of carbon disulfide were added and stirring was continued for 30 minutes at 10° C. 55 Parts of ethyl 3-aminopyrrolidinecarboxylate were added and the whole was stirred for 30 minutes at 10° C. 34.8 Parts of ethyl carbonochloridate were added dropwise (exothermic reaction) and stirring was continued for 4 hours at 60° C. After cooling, the product was extracted with methylbenzene. The extract was washed twice with water, dried, filtered and evaporated. The residue was purified by column chromatography over silica gel using a mixture of dichloromethane and ethanol (99:1 and 100:0.5 by volume) as eluents. The pure fractions were collected and the eluent was evaporated at a warm water bath at 30° C., yielding 25 parts (39.0%) of ethyl 3-isothiocyanato-1-pyrrolidinecarboxylate as a residue (interm. 6).

a-3) To a stirred and cooled (10° C.) mixture of 37 parts of N,N-methanetetraylbis[cyclohexanamine] and 594 parts of tetrahydrofuran were added 91.2 parts of carbon disulfide. After cooling to −10° C., 27.5 parts of ethyl 3-aminopyrrolidinecarboxylate were added during a period of 5 minutes (exothermic reaction). The reaction mixture was allowed to reach room temperature and evaporated. The residue was purified by column chromatography over silica gel using trichloromethane as eluent. The pure fractions were collected and the eluent was evaporated, yielding 32 parts (99.8%) of ethyl 3-isothiocyanato-1-pyrrolidinecarboxylate as a residue (interm. 6).

a-4) A mixture of 8.6 parts of sodium hydroxide and 120 parts of water was stirred at a temperature below 10° C. and there were added successively 17 parts of carbon disulfide and 35 parts of ethyl 3-amino-1-pyrrolidinecarboxylate. Stirring was continued for 3 hours. Then there were added dropwise 23.5 parts of ethyl carbonochloridate. Upon completion, stirring was continued for 2 hours at 60° C. The reaction mixture was extracted with methylbenzene. The extract was dried, filtered and evaporated, yielding 55 parts (100%) of ethyl 3-isothiocyanato-1-pyrrolidinecarboxylate as a residue (interm. 6).

b) A mixture of 80 parts of ethyl 3-isothiocyanato-1-pyrrolidinecarboxylate, 88.8 parts of $N^1$-[(5-methyl-2-furanyl)methyl]-1,2-benzenediamine and 560 parts of tetrahydrofuran was stirred for 2 hours at reflux temperature. After cooling to room temperature, the reaction mixture was evaporated, yielding 144.9 parts (100%) of ethyl 3-[[[[2-[[(5-methyl-2-furanyl)methyl]amino]phenyl]amino]thioxomethyl]amino]-1-pyrrolidinecarboxylate as a residue (interm. 7). In a similar manner there were also prepared:

b) A mixture of 34 parts of ethyl 3-[[[(2-nitrophenyl)amino]thioxomethyl]amino]-1-pyrrolidinecarboxylate, 56 parts of iron-powder, 2 parts of ammonium chloride, 160 parts of methanol and 30 parts of water was stirred and acidified with hydrochloric acid. Stirring was continued for 2 hours at reflux temperature. The reaction mixture was filtered over diatomaceous earth and the filtrate was evaporated, yielding 30 parts (97.5%) of ethyl 3-[[[(2-aminophenyl)amino]thioxomethyl]amino]-1-pyrrolidinecarboxylate as a residue (interm. 23).

Example 4 a) A mixture of 56 parts of ethyl hexahydro-4-oxo-1H-azepinecarboxylate, 40 parts of ethyl 2-cyanoacetate, 60 parts of N,N-diethylethanamine, 400 parts of methanol and 3 parts of thiophene in methanol 4% was hydrogenated at normal pressure and at room temperature with 4 parts of palladium-on-charcoal catalyst 10%. After the calculated amount of hydrogen was taken up, the catalyst was filtered off and the filtrate was evaporated, yielding 84.6 parts (99.8%) of ethyl α-cyano-1-(ethoxycarbonyl)hexahydro-1H-azepine-4-acetate as a residue (int. 24).

b) A mixture of 84.6 parts of ethyl α-cyano-1-(ethoxycarbonyl)hexahydro-1H-azepine-4-acetate, 300 parts of dimethyl sulfoxide and 15 parts of water was stirred and heated for 5 hours in an oil bath at 150° C. while ethanol was distilled off. The excess of dimethyl sulfoxide was distilled off and the residue was taken up in water. The product was extracted with dichloromethane. The extract was washed with water, dried, filtered and evaporated. The residue was distilled at 13.30 Pa, yielding 43.2 (66.5%) of ethyl 4-(cyanomethyl)hexahydro-1H-azepinecarboxylate; bp. 125° C. (int. 25).

c) Through a stirred mixture of 21 parts of ethyl

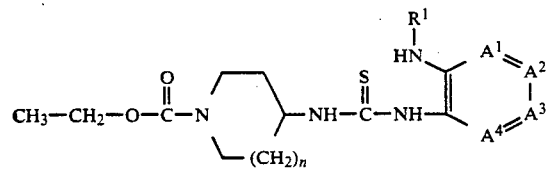

| Int. No. | n | $R^1$ | $A^1=A^2-A^3=A^4$ | base | mp (°C.) salt |
|---|---|---|---|---|---|
| 8 | 0 | 2-pyridinylmethyl | N=CH—CH=CH | HCl | 190 |
| 9 | 0 | 2-thienylmethyl | N=CH—CH=CH | HCl | 140 |
| 10 | 0 | 2-furanylmethyl | N=CH—CH=CH | base | residue |
| 11 | 0 | (5-methyl-2-furanyl)methyl | N=CH—CH=CH | base | residue |
| 12 | 2 | (5-methyl-2-furanyl)methyl | CH=CH—CH=CH | base | residue |
| 13 | 2 | (4-fluorophenyl)methyl | N=CH—N=CH | base | residue |
| 14 | 2 | H | CH=CH—CH=CH | base | residue |
| 15 | 2 | (4-fluorophenyl)methyl | CH=C(OCH$_3$)—CH=CH | base | residue |
| 16 | 2 | (4-fluorophenyl)methyl | CH=CH—N=CH | base | residue |
| 17 | 2 | (4-fluorophenyl)methyl | CH=CH—C(OCH$_3$)=CH | base | residue |
| 18 | 2 | (4-fluorophenyl)methyl | CH=CH—CH=N | base | residue |
| 19 | 2 | (4-fluorophenyl)methyl | CH=CH—C(CH$_3$)=CH | base | residue |
| 20 | 2 | (5-methyl-2-furanyl)methyl | CH=N—CH=CH | base | residue |
| 21 | 2 | H | CH=C(F)—C(F)=CH | base | residue |

Example 3 a) A mixture of 15.8 parts of ethyl 3-amino-1-pyrrolidinecarboxylate, 18 parts of 1-isothiocyanato-2-nitrobenzene and 180 parts of tetrahydrofuran was stirred for 1 hour at room temperature. The reaction mixture was evaporated, yielding 34 parts (100%) of ethyl 3[[[(2-nitrophenyl)amino]thioxomethyl]amino]-1-pyrrolidinecarboxylate as a residue (int. 22).

4-(cyanomethyl)hexahydro-1H-azepinecarboxylate, 5.06 parts of ethanol and 97.5 parts of trichloromethane was bubbled gaseous hydrogen chloride. The whole was allowed to stand over weekend in an ice box and then evaporated, yielding 29.2 parts (100%) of ethyl 4-(2-ethoxy-2-iminoethyl)hexahydro-1H-azepine-1-carboxylate monohydrochloride (int. 26).

Example 5 a) A mixture of 46 parts of ethyl hexahydro-4-oxo-1H-azepine-1-carboxylate, 26 parts of benzenemethanamine, 2 parts of a solution of thiophene in methanol 4% and 400 parts of methanol was hydrogenated at normal pressure and at room temperature with 4 parts of palladium-on-charcoal catalyst 10%. After the calculated amount of hydrogen was taken up, the catalyst was filtered off and the filtrate was evaporated, yielding 69.1 parts (100%) of ethyl hexahydro-4-[(phenylmethyl)amino]-1H-azepine-1-carboxylate as a residue (interm. 27).

b) 69.1 Parts of ethyl hexahydro-4-[(phenylmethyl)amino]-1H-azepine-1-carboxylate were hydrogenated in the prescence of a solution of thiophene in methanol at normal pressure and at room temperature with 4 parts of palladium-on-charcoal catalyst 10%. After the calculated amount of hydrogen was taken up, the catalyst was filtered off and the filtrate was evaporated, yielding 46.9 parts (100%) of ethyl 4-aminohexahydro-1H-azepine-1-carboxylate as a residue (interm. 28).

c) To a stirred and cooled (−10° C.) mixture of 63 parts of carbon disulfide, 52.1 parts of N,N'-methanetetraylbis[cyclohexanamine] and 360 parts of tetrahydrofuran were added dropwise 46.9 parts of ethyl 4-aminohexahydro-1H-azepine-1-carboxylate. Upon complete addition, the reaction mixture was stirred for 2 hours at room temperature. The reaction mixture was evaporated and the residue was stirred in 2,2'-oxybispropane. The precipitate was filtered off and the filtrate was evaporated, yielding 70.75 parts (100%) of ethyl hexahydro-4-isothiocyanato-1H-azepine-1-carboxylate as a residue (interm. 29).

d) A mixture of 119 parts of ethyl hexahydro-4-isothiocyanato-1H-azepine-1-carboxylate, 95.4 parts of N2-[(5-methyl-2-furanyl)methyl]-2,3-pyridinediamine and 810 parts of tetrahydrofuran was stirred for 6 hours at reflux temperature. After cooling, the reaction mixture was evaporated, yielding 203 parts (100.0%) of ethyl hexahydro-4-[[[[2-[[(5-methyl-2-furanyl)methyl]amino]-3-pyridinyl]amino]thioxomethyl]amino]-1H-azepine-1-carboxylate as a residue (interm. 30).

Example 6

To a stirred mixture of 23.5 parts of N-(4-fluorophenylmethyl)-1,2-benzenediamine and 14.4 parts of concentrated hydrochloric acid were added dropwise 9 parts of cyanamide at 100° C. After stirring for 3 hours at 100° C., there were added dropwise 10.5 parts of a sodium hydroxide solution 50%. Upon completion, stirring was continued overnight at reflux temperature. The reaction mixture was cooled and taken up in a mixture of water, trichloromethane and N,N-dimethylformamide. The organic phase was separated, dried, filtered and evaporated. The residue was stirred in trichloromethane. The product was filtered off and crystallized from trichloromethane, yielding 2.5 parts (9.5%) of 1-(4-fluorophenylmethyl)-1H-benzimidazol-2-amine; mp. 189.5° C. (int. 31).

Example 7

A mixture of 47.5 parts of N2-(2-furanylmethyl)-2,3-pyridinediamine, 36.5 parts of methyl (iminomethoxymethyl)carbamate, 34.5 parts of acetic acid and 450 parts of methylbenzene was stirred and heated for 16 hours at 65°~68° C. The reaction mixture was evaporated. 140 Parts of potassium hydroxide, 50 parts of water and 400 parts of 2-propanol were added to the residue and stirring was continued for 16 hours at reflux. The reaction mixture was concentrated to ¼ of its volume. 500 Parts of water were added and 2-propanol was distilled off azeotropically. After stirring for 1 hour at room temperature, the product was filtered off, washed successively twice with 20 parts of water and three times with 12 parts of 2-propanone and crystallized from 1,2-dichloroethane. The product was filtered off and dried in vacuo at 50° C., yielding 27.3 parts (51.0%) of 3-(2-furanylmethyl)-3H-imidazo[4,5-b]pyridin-2-amine; mp. 193.3° C. (interm. 32).

In a similar manner there was also prepared: 1-(2-furanylmethyl)-1H-benzimidazol-2-amine as a residue (int. 33).

B. Preparation of Final compounds

Example 8

A mixture of 176.5 parts of ethyl 3-[[[[2-[(4-thiazolylmethyl)amino]-3-pyridinyl]amino]thioxomethyl]amino]-1-pyrrolidinecarboxylate dihydrochloride, 163.0 parts of mercury(II) oxide, 0.1 parts of sulfur and 480 parts of methanol, saturated with ammonia was stirred for 1 hour at reflux temperature. The reaction mixture was filtered over diatomaceous earth while hot, washed with boiling methanol and the filtrate was evaporated. The residue was converted into the (E)-2-butenedioate salt in 1600 parts of 2-propanone. The salt was filtered off, washed with 2,2'-oxybispropane and dried in vacuo at 40° C., yielding 157.0 parts (77.6%) of ethyl 3-[[3-(4-thiazolylmethyl)-3H-imidazo[4,5-b]pyridin-2-yl]amino]-1-pyrrolidinecarboxylate (E)-2-butenedioate(2:3); mp. 150° C. (compound 1).

In a similar manner there were also prepared:
ethyl 3-(1H-benzimidazol-2-ylamino)-1-pyrrolidinecarboxylate monohydrochloride as a residue (compound 2);
ethyl 3-[[3-(2-pyridinylmethyl)-3H-imidazo[4,5-b]pyridin-2-yl]amino]-1-pyrrolidinecarboxylate as a residue (compound 3);
ethyl 3-[[3-(2-thienylmethyl)-3H-imidazo[4,5-b]pyridin-2-yl]amino]-1-pyrrolidinecarboxylate as a residue (compound 4);
ethyl 3-[[3-(2-furanylmethyl)-3H-imidazo[4,5-b]pyridin-2-yl]amino]-1-pyrrolidinecarboxylate as a residue (compound 5);
ethyl 3-[[3-[(5-methyl-2-furanyl)methyl]-3H-imidazo[4,5-b]pyridin-2-yl]amino]-1-pyrrolidinecarboxylate as a residue (compound 6);
ethyl 3-[[1-[(5-methyl-2-furanyl)methyl]-1H-benzimidazol-2yl]amino]-1-pyrrolidinecarboxylate as a residue (compound 7);
ethyl hexahydro-4-[[1-[(5-methyl-2-furanyl)methyl]-1H-benzimidazol-2-yl]amino]-1H-azepine-1-carboxylate as a residue (compound 8); and
ethyl hexahydro-4-[[3-[(5-methyl-2-furanyl)methyl]-3H-imidazo[4,5-b]pyridin-2yl]amino]-1H-azepine-1-carboxylate as a residue (compound 9).

Example 9

A mixture of 33.6 parts of ethyl 4-[[[(2-aminophenyl)amino]thioxomethyl]amino]hexahydro-1H-azepine-1-carboxylate, 26 parts of mercury(II) oxide, 0.1 parts of sulfur and 450 parts of tetrahydrofuran was stirred for 3 hours at reflux temperature. The reaction mixture was filtered while hot over diatomaceous earth and the filtrate was evaporated. The residue was boiled in acetonitrile. The product was filtered off and dried, yielding 24.5 parts (81.0%) of ethyl 4-(1H-benzimidazol-2-ylamino)hexahydro-1H-azepine-1-carboxylate; mp. 174.6° C. (compound 10).

In a similar manner there were also prepared:

ethyl 4-[[1-[(4-fluorophenyl)methyl]-6-methoxy-1H-benzimidazol-2-yl]amino]hexahydro-1H-azepine-1-carboxylate; mp. 157.6° C. (compound 11);

ethyl 4-[[1-[(4-fluorophenyl)methyl]-1H-imidazo[4,5-c]pyridin-2-yl]amino]hexahydro-1H-azepine-1-carboxylate as a residue (compound 12);

ethyl 4-[[1-[(4-fluorophenyl)methyl]-5-methoxy-1H-benzimidazol-2-yl]amino]hexahydro-1H-azepine-1-carboxylate as a residue (compound 13);

ethyl hexahydro-4-[[3-[(5-methoxy-2-furanyl)methyl]-3H-imidazo[4,5-c]pyridin-2-yl]amino]-1H-azepine-1-carboxylate as a residue (compound 14);

ethyl 4-[[1-[(4-fluorophenyl)methyl]-5-methyl-1H-benzimidazol-2-yl]amino]hexahydro-1H-azepine-1-carboxylate as a residue (compound 15); and ethyl 4-[[5,6-difluoro-1H-benzimidazol-2-yl]amino]hexahydro-1H-azepine-1-carboxylate as a residue (compound 16).

Example 10

A mixture of 74 parts of ethyl 4-[[[[4-[[(4-fluorophenyl)methyl]amino]-5-pyrimidinyl]amino]thioxomethyl]amino]hexahydro-1H-azepine-1-carboxylate, 39 parts of mercury(II) oxide and 240 parts of ethanol was stirred for 1 hour at reflux temperature. The reaction mixture was filtered while hot over diatomaceous earth and the filtrate was evaporated. The residue was taken up in water and the product was extracted with dichloromethane. The extract was dried, filtered and evaporated. The residue was crystallized from a mixture of 1,1'-oxybisethane and acetonitrile. The product was filtered off and dried, yielding 29 parts (46.8%) of ethyl 4-[[9-[(4-fluorophenyl)methyl]-9H-purin-8-yl]amino]-hexahydro-1H-azepine-1-carboxylate; mp. 156.7° C. (compound 17).

In a similar manner there was also prepared:

ethyl 4-[[1-[(4-fluorophenyl)methyl]-1H-imidazo[4,5-b]pyridin-2-yl]amino]hexahydro-1H-azepine-1-carboxylate as a residue (compound 18).

Example 11

A mixture of 18.25 parts of ethyl 4-(2-ethoxy-2-iminoethyl)hexahydro-1H-azepine-1-carboxylate monohydrochloride, 10.15 parts of N²-[(5-methyl-2-furanyl)methyl]-2,3-pyridinediamine and 200 parts of methanol was stirred and refluxed for 48 hours. After evaporation, the residue was taken up in water and made alkaline with potassium carbonate. The product was extracted with methylbenzene. The extract was dried, filtered and evaporated, yielding 21.3 parts (100%) of ethyl hexahydro-4-[[3-[(5-methyl-2-furanyl)methyl]-3H-imidazo[4,5-b]pyridin-2-yl]methyl]-1H-azepine-1-carboxylate as a residue (compound 19).

Example 12

A mixture of 33.3 parts of ethyl hexahydro-4-oxo-1H-azepine-1-carboxylate, 36.15 parts of 1-(4-fluorophenyl-methyl)-1H-benzimidazol-2-amine, 320 parts of methylbenzene and 0.1 parts of 4-methylbenzenesulfonic acid was stirred overnight at reflux temperature using a water separator. After cooling to 50° C., 80 parts of ethanol were added. 4.2 Parts of sodium tetrahydroborate were added portionwise and upon completion, stirring was continued for 2 hours at 50° C. After cooling, water and 4.8 parts of methanol were added while stirring. The layers were separated and the aqueous layer was extracted with methylbenzene. The combined organic layers were dried, filtered and evaporated, yielding 73 parts (100%) of ethyl 4-[[1-[(4-fluorophenyl)methyl]-1H-benzimidazol-2-yl]amino]hexahydro-1H-azepine-1-carboxylate as a residue (compound 20).

In a similar manner there was also prepared:

ethyl 4-[[3-(2-furanylmethyl)-3H-imidazo[4,5-b]pyridin-2-yl]amino]hexahydro-1H-azepine-1-carboxylate as an oily residue (compound 21); and ethyl 4-[[1-(2-furanylmethyl)-1H-benzimidazol-2-yl]amino]hexahydro-1H-azepine-1-carboxylate (E)-2-butenedioate(1:1); mp. 189.2° C. (compound 22).

Example 13

To a stirred mixture of 167 parts of ethyl 3-(1H-benzimidazol-2-ylamino)-1-pyrrolidinecarboxylate and 2790 parts of N,N-dimethylacetamide were added portionwise 61.0 parts of a sodium hydride dispersion 50%. Upon completion, stirring was continued for 1 hour at 50° C. 127.2 Parts of 2-(chloromethyl)pyridine hydrochloride were added portionwise at 80° C. After complete addition, the whole was stirred for 2 hours at 80° C. After cooling, the reaction mixture was poured into 1000 parts of water. The product was extracted twice with methylbenzene. The combined extracts were washed with water, dried, filtered and evaporated. The residue was purified twice by column chromatography over silica gel using a mixture of trichloromethane and methanol (95:5 and 99:1 by volume) as eluents. The first and second fractions were collected and the eluent was evaporated. The residue was converted into the hydrochloride salt in 2-propanol and 2,2'-oxybispropane. The salt was filtered off and dried, yielding 69.5 (24%) parts of ethyl 3-[[1-(2-pyridinylmethyl)-1H-benzimidazol-2-yl]amino]-1-pyrrolidinecarboxylate dihydrochloride; mp. >140° C. (compound 23).

In a similar manner there were also prepared:

ethyl 3-[[1-(2-pyrazinylmethyl)-1H-benzimidazol-2-yl]amino]-1-pyrrolidinecarboxylate as a residue (compound 24);

1-[(2,4-dichlorophenyl)methyl]-N-(hexahydro-1-methyl-1H-azepin-4-yl)-1H-benzimidazol-2-amine; mp. 131.8° C. (compound 25); and 1-[(4-chlorophenyl)methyl]-N-(hexahydro-1-methyl-1H-azepin-4-yl)-1H-benzimidazol-2-amine; mp. 106.9° C. (compound 26).

Example 14

A mixture of 6 parts of ethyl 4-(1H-benzimidazol-2-ylamino)hexahydro-1H-azepine-1-carboxylate, 3.75 parts of 4-(chloromethyl)thiazole hydrochloride, 5.3 parts of sodium carbonate and 90 parts of N,N-dimethylformamide was stirred overnight at 70° C. Another amount of 4-(chloromethyl)thiazole hydrochloride and sodium carbonate were added and stirring was continued overnight at 70° C. After cooling, the reaction mixture was poured into water. The product was extracted with methylbenzene. The extract was dried, filtered and evaporated. The residue was purified by column chromatography over silica gel using a mixture of trichloromethane and methanol (95:5 by volume) as eluent. The pure fractions were collected and the eluent was evaporated. The residue was converted into the (E)-2-butenedioate salt in ethanol. The salt was filtered off and dried, yielding 1.4 parts (13.5%) of ethyl hexahydro-4-[[1-(4-thiazolylmethyl)-1H-benzimidazol-2-yl]amino]-1H-azepine-1-carboxylate (E)-2-butenedioate (1:1); mp. 143.7° C. (compound 27).

In a similar manner there were also prepared:
ethyl hexahydro-4-[[1-(phenylmethyl)-1H-benzimidazol-2-yl]amino-1H-azepine-1-carboxylate as a residue (compound 28);
ethyl hexahydro-4-[[1-(2-thienylmethyl)-1H-benzimidazol-2-yl]amino]-1H-azepine-1-carboxylate as a residue (compound 29); and
ethyl 4-[[1-[bis(4-fluoropehnyl)methyl]-1H-benzimidazol-2-yl]amino]hexahydro-1H-azepine-1-carboxylate as a residue (compound 30).

In a similar manner there is also prepared:
ethyl hexahydro-4-[[1-(3-thienylmethyl)-1H-benzimidazol-2-yl]amino]-1H-azepine-1-carboxylate (compound 31).

Example 15

To a stirred mixture of 5.5 parts of ethyl 3-(1H-benzimidazol-2-ylamino)-1-pyrrolidinecarboxylate, 6.4 parts of sodium carbonate, 0.1 parts of potassium iodide and 81 parts of N,N-dimethylacetamide were added portionwise 4.3 parts of 4-(chloromethyl)thiazole hydrochloride at 130° C. Upon completion, stirring was continued for 3 hours at 130° C. After cooling, the reaction mixture was poured into 450 parts of water. The product was extracted twice with methylbenzene. The combined extracts were washed with water, dried, filtered and evaporated, yielding 5.2 parts (69.9%) of ethyl 3-[[1-(4-thiazolylmethyl)-1H-benzimidazol-2-yl]amino]-1-pyrrolidinecarboxylate as an oily residue (compound 32).

In a similar manner there were also prepared:
ethyl 3-[[1-(2-thienylmethyl)-1H-benzimidazol-2-yl]amino]-1-pyrrolidinecarboxylate as an oily residue (compound 33); and
ethyl 4-[(1-ethyl-1H-benzimidazol-2-yl)amino]hexahydro-1H-azepine-1-carboxylate as a residue (compound 34).

Example 16

A mixture of 11 parts of ethyl 4-[[5,6-difluoro-1H-benzimidazol-2-yl]amino]hexahydro-1H-azepine-1-carboxylate, 7.2 parts of 1-(chloromethyl)-4-fluorobenzene, 3.2 parts of sodium carbonate and 90 parts of N,N-dimethylformamide was stirred and heated for 24 hours at 80° C. The reaction mixture was evaporated and the residue was taken up in water. The product was extracted with dichloromethane. The extract was dried, filtered and evaporated. The residue was purified by column chromatography over silica gel using trichloromethane as eluent. The pure fractions were collected and the eluent was evaporated, yielding 6 parts (40.6%) of ethyl 4-[[5,6-difluoro-1-[(4-fluorophenyl)methyl]-1H-benzimidazol-2-yl]amino]hexahydro-1H-azepine-1-carboxylate as a residue; (compound 35).

In a similar manner there were also prepared:
ethyl 3-[1-(4-fluorophenylmethyl)-1H-benzimidazol-2-ylamino]-1-pyrrolidinecarboxylate as a residue (compound 36); and
ethyl hexahydro-4-[[1-[(4-methylphenyl)methyl]-1H-benzimidazol-2-yl]amino]-1H-azepine-1-carboxylate as a residue (compound 37).

Example 17

A mixture of 157.0 parts of ethyl 3-[[3-(4-thiazolylmethyl)-3H-imidazo[4,5-b]pyridin-2-yl]amino]-1-pyrrolidinecarboxylate (E)-2-butenedioate(2:3) and 870 parts of a hydrobromic acid solution 48% in water was stirred for 22 hours at 100° C. After cooling, the precipitate was filtered off and washed with water. The filtrate was evaporated. The residue was taken up three times in methylbenzene and the solvent was evaporated each time. The oily residue was stirred in 2-propanone. The precipitate was filtered off and the filtrate was evaporated. The residue was taken up in boiling ethanol. The clear solution was filtered and the filtrate was allowed to crystallize over weekend while stirring. The crystallized product was filtered off, washed with ethanol and dried in vacuo at 50° C., yielding 106.5 parts (79.4%) of N-(3-pyrrolidinyl)-3-(4-thiazolylmethyl)-3H-imidazo[4,5-b]pyridin-2-amine dihydrobromide; mp. 260.5° C. (compound 38).

In a similar manner there were also prepared:
1-[(4-fluorophenyl)methyl]-N-(3-pyrrolidinyl)-1H-benzimidazol-2-amine as a residue (compound 39);
N-(3-pyrrolidinyl)-1-(4-thiazolylmethyl)-1H-benzimidazol-2-amine dihydrobromide.hemihydrate; mp. 214.7° C. (compound 40);
1-[(2-pyrazinyl)methyl]-N-(3-pyrrolidinyl)-1H-benzimidazol-2-amine as a residue (compound 41);
1-(2-pyridinylmethyl)-N-(3-pyrrolidinyl)-1H-benzimidazol-2-amine dihydrochloride; mp. >260° C. (compound 42);
3-(2-pyridinylmethyl)-N-(3-pyrrolidinyl)-3H-imidazo[4,5-b]pyridin-2-amine trihydrobromide; mp. 253.5° C. (compound 43);
1-[(4-fluorophenyl)methyl]-N-(hexahydro-1H-azepin-4-yl)-1H-benzimidazol-2-amine dihydrochloride; mp. 193.3° C. (compound 44);
9-[(4-fluorophenyl)methyl]-N-(hexahydro-1H-azepin-4-yl)-9H-purin-8-amine dihydrochloride,hemihydrate; mp. 240.0° C. (compound 45);
1-[(4-fluorophenyl)methyl]-N-(hexahydro-1H-azepin-4-yl)-1H-imidazo[4,5-c]pyridin-2-amine; mp. 203.0° C. (compound 46); and
1-[(4-fluorophenyl)methyl]-N-(hexahydro-1H-azepin-4-yl)-1H-imidazo[4,5-b]pyridin-2-amine monohydrochloride; mp. 212.6° C. (compound 47).

Example 18

A mixture of 188 parts of ethyl hexahydro-4-[[(5-methyl-2-furanyl)methyl]-1H-benzimidazol-2-yl]amino]-1H-azepine-1-carboxylate, 166.5 parts of potassium hydroxide, 18 parts of water and 1440 parts of 2-propanone was stirred for 18 hours at reflux temperature. After cooling, another portion of 166.5 parts of potassium hydroxide was added and stirring was continued for 6 hours at reflux. After cooling, the reaction mixture was evaporated and the residue was stirred in 1500 parts of water. The product was extracted three times with dichloromethane. The extract was dried, filtered and evaporated. The residue was converted into the (E)-2-butenedioate salt in 2000 parts of 2-propanone and 800 parts of ethanol. The reaction mixture was allowed to cool while stirring. The precipitated product was filtered off, washed with 2-propanone and crystalized from a mixture of 2-propanone and ethanol (1:2 by volume). The product was filtered off, washed with 2-propanone and dried in vacuo at 50° C., yielding 132.6 parts (52.9%) of N-(hexahydro-1H-azepin-4-yl)-1-[(5- methyl-2-furanyl)methyl]-1H-benzimidazol-2-amine (E)-2-butenedioate(2:3).trihydrate; mp. 115.2° C. (compound 48).

In a similar manner there were also prepared:

3-(2-furanylmethyl)-N-(hexahydro-1H-azepin-4-yl)-3H-imidazo[4,5-b]pyridin-2-amine dihydrochloride; mp. 253.1° C. (compound 49);

N-(hexahydro-1H-azepin-4-yl)-3-[(5-methyl-2-furanyl)methyl]-3H-imidazo[4,5-b]-pyridin-2-amine ethanedioate(1:2); mp. 140° C. (compound 50);

N-(hexahydro-1H-azepin-4-yl)-3-[(5-methyl-2-furanyl)methyl]-3H-imidazo[4,5-c]pyridin-2-amine (E)-2-butenedioate (2:5) hemihydrate; mp. 141.4° C. (compound 51);

2-[(hexahydro-1H-azepin-4-yl)methyl]-3-[(5-methyl-2-furanyl)methyl]-3H-imidazo[4,5-b]pyridine (E)-2-butenedioate (2:3) monohydrate; mp. 130.6° C. (compound 52);

N-(3-pyrrolidinyl)-1-(2-thienylmethyl)-1H-benzimidazol-2-amine as a residue (compound 53);

N-(3-pyrrolidinyl)-3-(2-thienylmethyl)-3H-imidazo[4,5-b]pyridin-2-amine dihydrochloride; mp. 140° C. (compound 54);

3-(2-furanylmethyl)-N-(3-pyrrolidinyl)-3H-imidazo[4,5-b]pyridin-2-amine (E)-2-butenedioate(2:3); mp. 170° C. (compound 55);

3-(2-furanylmethyl)-N-(3-pyrrolidinyl)-3H-imidazo[4,5-b]pyridin-2-amine dihydrochloride,2-propanolate(2:1) mp. >300° C. (compound 56);

3-[(5-methyl-2-furanyl)methyl]-N-(3-pyrrolidinyl)-3H-imidazo[4,5-b]pyridin-2-amine ethanedioate(1:2) as a residue (compound 57); and 1-[(5-methyl-2-furanyl)methyl]-N-(3-pyrrolidinyl)-1H-benzimidazol-2-amine monohydrochloride; mp. 190° C. (compound 58).

Example 19

A mixture of 4.2 parts of 3-(2-chloroethyl)-6,7,8,9-tetrahydro-2-methyl-4H-pyrido[1,2-a]pyrimidin-4-one monohydrochloride, 6.9 parts of N-(3-pyrrolidinyl)-1-(4-thiazolylmethyl)-1H-benzimidazol-2-amine dihydrobromide, 9.7 parts of sodium carbonate, 0.1 parts of potassium iodide and 90 parts of N,N-dimethylacetamide was stirred for 1.5 hour at 100° C. After cooling, the reaction mixture was poured into 500 parts of water. The product was extracted three times with dichloromethane. The combined extracts were washed with water, dried, filtered and evaporated. The oily residue was converted into the (E)-2-butenedioate salt in 180 parts of 2-propanone and ethanol. The salt was filtered off and dried, yielding 6 parts (51.2%) of 6,7,8,9-tetrahydro-2-methyl-3-[2-[3-[[1-(4-thiazolylmethyl)-1H-benzimidazol-2-yl]amino]-1-pyrrolidinyl]ethyl]-4H-pyrido[1,2-a]pyrimidin-4-one (E)-2-butenedioate (2:5); mp. 148.1° C. (compound 59).

In a similar manner there were also prepared:

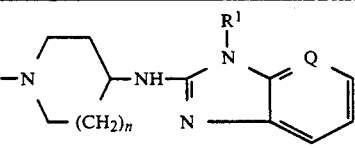

| No. | L | n | R¹ | Q | salt base | mp. (°C.) |
|---|---|---|---|---|---|---|
| 60 | 4-CH₃O—C₆H₄—(CH₂)₂— | 0 | 2-pyridinylmethyl | CH | * | 174.4 |
| 61 | 4-CH₃O—C₆H₄—(CH₂)₂— | 0 | 2-pyridinylmethyl | N | 2(COOH)₂ 0.5H₂O | 156.5 |
| 62 | 4-CH₃O—C₆H₄—(CH₂)₂— | 0 | 2-thienylmethyl | CH | 2(COOH)₂ | 192.6 |
| 63 | CH₃—CH₂—O—C(=O)—NH—(CH₂)₂— | 0 | 2-thienylmethyl | CH | 2(COOH)₂ | 170 |
| 64 | 4-CH₃O—C₆H₄—(CH₂)₂— | 0 | 5-methyl-2-furanylmethyl | N | 2(COOH)₂ | 160.0 |
| 65 | 4-CH₃O—C₆H₄—(CH₂)₂— | 0 | 4-thiazolylmethyl | N | 2(COOH)₂ | 173.1 |
| 66 | 4-CH₃O—C₆H₄—(CH₂)₂— | 2 | 4-F—C₆H₄—CH₂— | CH | 2(COOH)₂ | 192.3 |
| 67 | 4-CH₃O—C₆H₄—(CH₂)₂— | 2 | 5-methyl-2-furanylmethyl | CH | 1.5(COOH)₂ 0.5H₂O | 121.5 |
| 68 | 4-CH₃O—C₆H₄—(CH₂)₂— | 2 | 5-methyl-2-furanylmethyl | N | 2(COOH)₂ | 120.2 |
| 69 | H₃C—CH₂—N⟨(C=O)⟩N—(CH₂)₂— (N═N) | 2 | 5-methyl-2-furanylmethyl | N | ** | 113.9 |
| 70 | C₂H₅—O—(CH₂)₂— | 2 | 5-methyl-2-furanylmethyl | N | — | — |
| 71 | 2-thienyl-(CH₂)₂— | 2 | 5-methyl-2-furanylmethyl | N | 2(COOH)₂ | 179.0 |
| 72 | 2-pyridinyl-(CH₂)₂— | 2 | 5-methyl-2-furanylmethyl | N | — | — |
| 73 | 4-F—C₆H₄—C(=O)—(CH₂)₃— | 2 | 5-methyl-2-furanylmethyl | N | 2(COOH)₂ | 153.2 |
| 74 | phthalimido-N—(CH₂)₂— | 2 | 5-methyl-2-furanylmethyl | N | — | — |

5,071,846

31

32

-continued

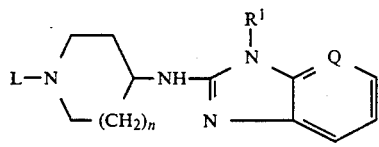

| No. | L | n | R¹ | Q | salt base | mp. (°C.) |
|---|---|---|---|---|---|---|
| 75 | [structure: dimethylxanthine-N-(CH₂)₂-] | 2 | 5-methyl-2-furanylmethyl | N | | — |
| 76 | [structure: thiazine with CH₃, (CH₂)₂-] | 2 | 5-methyl-2-furanylmethyl | N | | — |
| 77 | 4-morpholinyl-(CH₂)₂— | 2 | 5-methyl-2-furanylmethyl | N | | — |
| 78 | [structure: imidazolyl-NH-(CH₂)₂-] | 2 | 5-methyl-2-furanylmethyl | N | | — |
| 79 | [structure: pyrimidinone-N-(CH₂)₂-] | 2 | 5-methyl-2-furanylmethyl | N | | — |
| 80 | [structure: oxazolidinone-N-(CH₂)₂-] | 2 | 5-methyl-2-furanylmethyl | N | | — |
| 81 | CH₃—C(O)—(CH₂)₃— | 2 | 5-methyl-2-furanylmethyl | N | | — |
| 82 | CH₂=CH—CH₂— | 2 | 5-methyl-2-furanylmethyl | N | | — |
| 83 | C₆H₅—CH=CH—CH₂— | 2 | 5-methyl-2-furanylmethyl | N | | — |

* = (E)-2-butenedioate(2:5)
** = (E)-2-butenedioate(3:2) 2-propanolate(1:1)

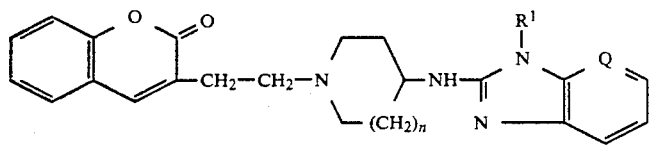

| Comp. No. | n | R¹ | Q | salt/base | mp. (°C.) |
|---|---|---|---|---|---|
| 84 | 0 | 4-thiazolylmethyl | CH | * | 207.2 |
| 85 | 0 | 2-pyridinylmethyl | CH | * 0.5H₂O | 208.0 |
| 86 | 0 | 2-pyridinylmethyl | N | 2HNO₃ | 160.3 |
| 87 | 0 | 2-thienylmethyl | CH | 2(COOH)₂ | 196.4 |
| 88 | 0 | 4-thiazolylmethyl | N | 2(COOH)₂ | 193.2 |
| 89 | 2 | 4-F—C₆H₄—CH₂— | CH | 2(COOH)₂/0.5H₂O | 194.3 |

* = (E)-2-butenedioate(2:3)

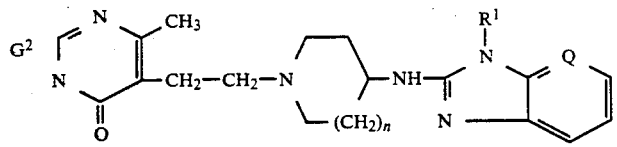

| No. | G² | n | R¹ | Q | salt/base | mp. (°C.) |
|---|---|---|---|---|---|---|
| 90 | CH=CH—CH=CH | 0 | 4-thiazolylmethyl | CH | (E)-2-butenedioate(2:3) | 204.8 |
| 91 | CH=CH—CH=CH | 0 | 2-pyridinylmethyl | CH | (E)-2-butenedioate(2:3) | 198.0 |
| 92 | CH=CH—CH=CH | 0 | 2-pyridinylmethyl | N | 4HCl 0.5 CH₃—CH(OH)—CH₃ | 284.2 |
| 93 | CH=CH—CH=CH | 0 | 2-thienylmethyl | CH | (E)-2-butenedioate(1:3) | 147.9 |
| 94 | CH=CH—CH=CH | 0 | 5-methyl-2-furanylmethyl | N | base | 168.0 |
| 95 | CH=CH—CH=CH | 0 | 4-thiazolylmethyl | N | (E)-2-butenedioate(2:3) | 214.9 |
| 96 | CH=CH—CH=CH | 0 | 5-methyl-2-furanylmethyl | CH | (E)-2-butenedioate(2:3) | 205.8 |
| 97 | (CH₂)₄ | 0 | 2-pyridinylmethyl | CH | (E)-2-butenedioate(2:3) | 200.9 |
| 98 | (CH₂)₄ | 0 | 2-thienylmethyl | CH | (E)-2-butenedioate(1:2) | 157.3 |
| 99 | (CH₂)₄ | 0 | 2-pyridinylmethyl | N | base | 152.2 |
| 100 | (CH₂)₄ | 0 | 5-methyl-2-furanylmethyl | N | (E)-2-butenedioate(2:3) | 191.6 |
| 101 | (CH₂)₄ | 0 | 4-thiazolylmethyl | N | (E)-2-butenedioate(2:3) | 201.3 |
| 102 | (CH₂)₄ | 0 | 5-methyl-2-furanylmethyl | CH | (E)-2-butenedioate(2:3) | 177.0 |
| 103 | CH=CH—CH=CH | 2 | 5-methyl-2-furanylmethyl | CH | 2 (COOH)₂/H₂O | 134.2 |

6-[2-[hexahydro-4-[[3-[(5-methyl-2-furanyl)methyl]-3H-imidazo[4,5-b]pyridin-2-yl]amino]-1H-azepin-1-yl]ethyl]-7-methyl-5H-thiazolo[3,2-a]pyrimidin-5-one ethanedioate (1:2); mp. 136.0° C. (compound 104); and and N-[1-[(2,3-dihydro-1,4-benzodioxin-2-yl)methyl]-hexahydro-1H-azepin-4-yl]-3-[(5-methyl-2-furanyl)methyl]-3H-imidazo[4,5-b]pyridin-2-amine (E)-2-butenedioate (1:2) (compound 105);

In a similar manner there are also prepared:

| Comp. No. | L | B | base/salt | mp. (°C.) |
|---|---|---|---|---|
| 106 | 4-CH₃O—C₆H₄—(CH₂)₂— | CH₂ | | |
| 107 | (structure: benzimidazolinone-N—(CH₂)₂—) | CH₂ | (E)-2-butenedioate(1:1) | 188.4 |
| 108 | (structure with pyridine-CH₃ and ring) | CH₂ | | |

Example 20

A mixture of 3.8 parts of 3-(2-bromoethyl)-2H-1-benzopyran-2-one, 4.7 parts of 3-(2-furanylmethyl)-N-(hexahydro-1H-azepin-4-yl)-3H-imidazo[4,5-b]pyridin-2-amine, 1.5 parts of sodium carbonate and 45 parts of N,N-dimethylacetamide was stirred for 48 hours at 80° C. After cooling, the reaction mixture was poured into water and the product was extracted with trichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the ethanedioate salt in ethanol. The salt was filtered off and dried, yielding 1 part (10%) of 3-[2-[4-[[3-(2-furanylmethyl)-3H-imidazo[4,5-b]pyridin-2-yl]amino]hexahydro-1H-azepin-1-yl]ethyl]-2H-1-benzopyran-2-one ethanedioate(1:2); mp. 179.7° C. (compound 109).

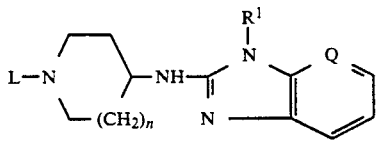

-continued

| No. | L | n | R¹ | Q | salt/base | mp. (°C.) |
|---|---|---|---|---|---|---|
| 110 | 4-CH₃O—C₆H₄—(CH₂)₂— | 0 | 2-thienylmethyl | N | (E)-2-butenedioate(1:1) | 190.4 |
| 111 | 4-CH₃O—C₆H₄—(CH₂)₂— | 2 | 2-furanylmethyl | N | 2 (COOH)₂ | 158.2 |
| 112 | 2-oxo-2H-1-benzo-pyran-3-ylethyl | 0 | 2-furanylmethyl | N | (E)-2-butenedioate(2:1) | 169.4 |
| 113 | 2-oxo-2H-1-benzo-pyran-3-ylethyl | 0 | 2-thienylmethyl | N | (E)-2-butenedioate(1:1) | 202.4 |

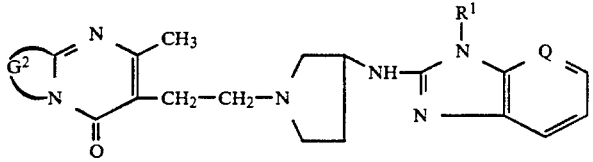

| No. | G² | R¹ | Q | salt/base | mp. (°C.) |
|---|---|---|---|---|---|
| 114 | CH=CH—CH=CH | 4-F—C₆H₄—CH₂— | CH | (E)-2-butenedioate(1:2) 2-propanol(2:1) | 180.0 |
| 115 | CH=CH—CH=CH | 2-furanylmethyl | N | (E)-2-butenedioate(2:3) | 190.0 |
| 116 | CH=CH—CH=CH | 2-thienylmethyl | N | (E)-2-butenedioate(2:3) | 227.4 |
| 117 | (CH₂)₄ | 2-furanylmethyl | N | (E)-2-butenedioate(2:3) | 210.5 |
| 118 | (CH₂)₄ | 2-thienylmethyl | N | (E)-2-butenedioate(2:3) | 221.2 |
| 119 | (CH₂)₄ | 2-furanylmethyl | N | (E)-2-butenedioate(1:3) | 164.7 | and 3-[2-[4-[[9-[(4-fluorophenyl)methyl]-9H-purin-8-yl]amino]hexahydro-1H-azepin-1-yl]ethyl]-2-methyl-4H-pyrido[1,2-a]pyrimidin-4-one (E)-2-butenedioate(1:2); mp. 210.5° C. (compound 120).

Example 21

A mixture of 3.1 parts of 1-(2-chloroethyl)-4-methoxybenzene, 6.9 parts of N-(3-pyrrolidinyl)-1-(4-thiazolylmethyl)-1H-benzimidazol-2-amine dihydrobromide,hemihydrate, 8.0 parts of sodium carbonate, 0.1 parts of potassium iodide and 120 parts of 4-methyl-2-pentanone was stirred for 22 hours at reflux temperature using a water separator. After cooling, the reaction mixture was poured into water. The organic phase was separated, washed with water, dried, filtered and evaporated. The residue was purified by column chromatography over silica gel using a mixture of trichloromethane, methanol and ammonium hydroxide (95:5:0.5 by volume) as eluent. The pure fractions were collected and the eluent was evaporated. The residue was converted into the ethanedioate salt in 2-propanone. After cooling, the precipitated product was filtered off and dried, yielding 2.0 parts (21.7%) of N-[1-[2-(4-methoxyphenyl) ethyl]-3-pyrrolidinyl]-1-(4-thiazolylmethyl)-1H-benzimidazol-2-amine ethanedioate(1:2); mp. 191.1° C. (compound 121).

In a similar manner there were also prepared:
3-[2-[3-[[1-[(4-fluorophenyl)methyl]-1H-benzimidazol-2-yl]amino]-1-pyrrolidinyl]ethyl]-6,7,8,9-tetrahydro-2-methyl-4H-pyrido[1,2-a]pyrimidin-4-one (E)-2-butenedioate(2:3),monohydrate; mp. 153.9° C. (compound 122);
N-[1-[2-(4-methoxyphenyl)ethyl]-3-pyrrolidinyl]-1-(2-pyrazinylmethyl)-1H-benzimidazol-2-amine ethanedioate(1:2); mp. 193.3° C. (compound 123); and
N-[1-[2-(4-methoxyphenyl)ethyl]-3-pyrrolidinyl]-1-[(5-methyl-2-furanyl)methyl]-1H-benzimidazol-2-amine ethanedioate(1:2); mp. 177.0° C. (compound 124).

Example 22

A mixture of 6.2 parts of 1-[(4-fluorophenyl)methyl]-N-(3-pyrrolidinyl)-1H-benzimidazol-2-amine, 4.3 parts of sodium carbonate and 120 parts of 4-methyl-2-pentanone was stirred and refluxed for 30 minutes using a water separator. 4.9 Parts of 1-(2-chloroethyl)-1,3-dihydro-2H-benzimidazol-2-one were added at reflux temperature and stirring was continued for 20 hours at reflux temperature using a water separator. After cooling, the salts were filtered off and the filtrate was washed with water, dried, filtered and evaporated. The residue was purified by column chromatography over silica gel using a mixture of trichloromethane, methanol and ammonium hydroxide (90:9:1 by volume) as eluent. The pure fractions were collected and the eluent was evaporated. The residue was converted into the ethanedioate salt in 2-propanone. The salt was filtered off and dried in a dry pistol with methylbenzene, yielding 6.30 parts (45%) of 1-[2-[3-[[1-[(4-fluorophenyl)methyl]-1H-benzimidazol-2-yl]amino]-1-pyrrolidinyl]ethyl]-1,3-dihydro-2H-benzimidazol-2-one ethanedioate(2:5); mp. 190.6° C. (compound 125).

In a similar manner there was also prepared:
3-[2-[3-[[1-[(4-fluorophenyl)methyl]-1H-benzimidazol-2-yl]amino]-1-pyrrolidinyl]ethyl]-2H-1-benzopyran-2-one ethanedioate(1:2); mp. 208.1° C. (compound 126).

Example 23

A mixture of 1.85 parts of (2-bromoethyl)benzene, 3.1 parts of 1-[(4-fluorophenyl)methyl]-N-(3-pyrrolidinyl)-1H-benzimidazol-2-amine, 1.06 parts of sodium carbonate, 0.1 parts of potassium iodide and 120 parts of N,N-dimethylformamide was stirred and heated overnight at 70° C. The reaction mixture was poured into water and the product was extracted with 4-methyl-2-pentanone. The extract was dried, filtered and evaporated. The residue was purified by column chromatography over silica gel using a mixture of trichloromethane and methanol (96:4 by volume) as eluent. The pure fractions were collected and the eluent was evaporated. The residue was crystallized from 2,2'-oxybispropane. The product was filtered off and dried, yielding 0.5 parts (12%) of 1-[(4-fluorophenyl)methyl]-N-[1-(2-phenylethyl)-3-pyrrolidinyl]-1H-benzimidazol-2-amine; mp. 126.1° C. (compound 127).

In a similar manner there were also prepared:
1-[(4-fluorophenyl)methyl]-N-[1-(3-phenoxypropyl)-3-pyrrolidinyl]-1H-benzimidazol-2-amine; mp. 104.7° C. (compound 128); and 1-[(4-fluorophenyl)methyl]-N-[1-[2-(4-methoxyphenyl)ethyl]-3-pyrrolidinyl]-1H-benzimidazol-2-amine; mp. 143.8° C. (compound 129).

Example 24

A mixture of 7.6 parts of 3-(2-bromoethyl)-2H-1-benzopyran-2-one, 6.0 parts of 3-[(5-methyl-2-furanyl)methyl]-N-(3-pyrrolidinyl)-3H-imidazo[4,5-b]pyridin-2-amine, 8.4 parts of sodium hydrogen carbonate, 0.1 parts of potassium iodide and 160 parts of ethanol was stirred for 4 hours at reflux temperature. After cooling to room temperature, the precipitated product was filtered off and the filtrate was evaporated. The residue was stirred in ethyl acetate. The precipitate was filtered off and the filtrate was evaporated. The residue was purified by column chromatography over silica gel using a mixture of trichloromethane, hexane, methanol and ammonium hydroxide (45:45:9:1 by volume) as eluent. The pure fractions were collected and the eluent was evaporated. The residue was converted into the (E)-2-butenedioate salt in 2-propanone. The salt was filtered off and crystallized twice from ethanol. The product was filtered off, washed with ethanol and dried in vacuo at 50° C., yielding 3 parts (25.6%) of 3-[2-[3-[[3-[(5-methyl-2-furanyl) methyl]-3H-imidazo[4,5-b]pyridin-2-yl]amino]-1-pyrrolidinyl]ethyl]-2H-1-benzopyran-2-one (E)-2-butenedioate(1:1); mp. 194.2° C. (compound 130).

In a similar manner there were also prepared:
3-[2-[3-[[1-(2-pyrazinylmethyl)-1H-benzimidazol-2-yl]amino]-1-pyrrolidinyl]ethyl]-2H-1-benzopyran-2-one (E)-2-butenedioate(2:3).hemihydrate; mp. 204.7° C. (compound 131); and
2-methyl-3-[2-[3-[[1-(2-pyrazinylmethyl)-1H-benzimidazol-2-yl]amino]-1-pyrrolidinyl]ethyl]-4H-pyrido[1,2-a]pyrimidin-4-one (E)-2-butenedioate(2:5); mp. 151.9° C. (compound 132).

Example 25

To a stirred and heated (60° C.) suspension of 14 parts of 1-(2-pyridinylmethyl)-N-(3-pyrrolidinyl)-1H-benzimidazol-2-amine dihydrochloride and 9.5 parts of sodium carbonate in 113 parts of N,N-dimethylformamide were added dropwise 3.2 parts of 2-chloroacetonitrile. Upon completion, stirring was continued for 3 hours at 60° C. After cooling, the mixture was poured into ice water and the product was extracted six times with methylbenzene. The combined organic layers were washed with water, dried, filtered and evaporated, yielding 11 parts (87%) of 3-[[1-(2-pyridinylmethyl)-1H-benzimidazol-2-yl]amino]-1-pyrrolidineacetonitrile as a residue (compound 133).

In a similar manner there were also prepared:
3-[[1-[(4-fluorophenyl)methyl]-1H-benzimidazol-2-yl]amino]-1-pyrrolidineacetonitrile as a residue (compound 134);
3-[[1-(2-pyrazinylmethyl)-1H-benzimidazol-2-yl]amino]-1-pyrrolidineacetonitrile (E)-2-butenedioate(1:1) (compound 135);
3-[[3-(2-pyridinylmethyl)-3H-imidazo[4,5-b]pyridin-2-yl]amino]-1-pyrrolidineacetonitrile; mp. 150° C. (compound 136); and
4-[[1-[(4-fluorophenyl)methyl]-1H-benzimidazol-2-yl]amino]hexahydro-1H-azepine-1-acetonitrile; mp. 130° C. (compound 137).

Example 26

A mixture of 11 parts of 3-[[1-(2-pyridinylmethyl)-1H-benzimidazol-2-yl]amino]-1-pyrrolidineacetonitrile and 320 parts of methanol, saturated with ammonia was hydrogenated at normal pressure and at room temperature with 3 parts of Raney-nickel catalyst. After the calculated amount of hydrogen was taken up, the catalyst was filtered off and the filtrate was evaporated. The residue was solidified in 2,2'-oxybispropane while stirring. The product was filtered off and dried, yielding 10 parts (91%) of N-[1-(2-aminoethyl)-3-pyrrolidinyl]-1-(2-pyridinylmethyl)-1H-benzimidazol-2-amine; mp. 130° C. (compound 138).

In a similar manner there were also prepared:
N-[1-(2-aminoethyl)-3-pyrrolidinyl]-1-[(4-fluorophenyl)methyl]-1H-benzimidazol-2-amine as a residue (compound 139);
N-[1-(2-aminoethyl)-3-pyrrolidinyl]-1-(2-pyrazinylmethyl)-1H-benzimidazol-2-amine as a residue (compound 140);
N-[1-(2-aminoethyl)-3-pyrrolidinyl]-3-(2-pyridinylmethyl)-3H-imidazo[4,5-b]pyridin-2-amine as a residue (compound 141); and
N-[1-(2-aminoethyl)hexahydro-1H-azepin-4-yl]-1-[(4-fluorophenyl)methyl]-1H-benzimidazol-2-amine as a residue (compound 142).

Example 27

A mixture of 16.8 parts of ethyl (2-chloroethyl)carbamate, 30 parts of N-(3-pyrrolidinyl)-3-(2-thienylmethyl)-3H-imidazo[4,5-b]pyridin-2-amine, 21.2 parts of sodium carbonate and 270 parts of N,N-dimethylacetamide was stirred for 5 hours at 100° C. After cooling, the reaction mixture was poured into ice water and the product was extracted five times with 4-methyl-2-pentanone. The combined extracts were washed with water, dried, filtered and evaporated. The residue was converted into the (E)-2-butenedioate salt in 2-propanol and 1,1'-oxybisethane. The salt was filtered off and dried, yielding 30 parts (56.5%) of ethyl [2-[3-[[3-(2-thienylmethyl)-3H-imidazo[4,5-b]pyridin-2-yl]amino]-1-pyrrolidinyl]ethyl]carbamate (E)-2-butenedioate(1:1); mp. 187.8° C. (compound 143).

In a similar manner there were also prepared:
ethyl [2-[3-[[1-(4-thiazolylmethyl)-1H-benzimidazol-2-yl]amino]-1-pyrrolidinyl]ethyl]carbamate as an oily residue (compound 144);
ethyl [2-[3-[[3-[(5-methyl-2-furanyl)methyl]-3H-imidazo[4,5-b]pyridin-2-yl]amino]-1-pyrrolidinyl]ethyl]carbamate (E)-2-butenedioate(1:2); mp. 165° C. (compound 145);
ethyl [2-[3-[[3-(4-thiazolylmethyl)-3H-imidazo[4,5-b]pyridin-2-yl]amino]-1-pyrrolidinyl]ethyl]carbamate as a residue (compound 146); and
ethyl [2-[hexahydro-4-[[1-[(5-methyl-2-furanyl)methyl]-1H-benzimidazol-2-yl]amino]-1H-azepin-1-yl]ethyl]carbamate as a residue (compound 147).

In a similar manner there is also prepared:
N-methyl-N'-[2-[hexahydro-4-[[1-[(5-methyl-2-furanyl)methyl]-3H-imidazo[4,5-b]pyridin-2-yl]amino]-1H-azepin-1-yl]ethyl]urea (compound 148).

Example 28

To a stirred mixture of 85 parts of potassium hydroxide, 5 parts of water and 368 parts of 2-propanol were added 50.5 parts of ethyl [2-[hexahydro-4-[[1-[(5-methyl-2-furanyl)methyl]-1H-benzimidazol-2-yl]amino]-1H- azepin-1-yl]ethyl]carbamate (exothermic reaction, the mixture was cooled when the temperature reached 60° C.). The reaction mixture was refluxed for 2 hours. After cooling, the mixture was evaporated. The residue was taken up in 800 parts of water and the product was extracted three times with dichloromethane. The combined extracts were washed with a small amount of water, dried, filtered and evaporated. The residue was converted into the (E)-2-butenedioate salt in 320 parts of ethanol. The salt was filtered off, washed with ethanol and dried in vacuo at 40° C., yielding 48.0 parts (55.8%) of N-[1-(2-aminoethyl)hexahydro-1H-azepin-4-yl]-1-[(5-methyl-2-furanyl)methyl]-1H -benzimidazol-2-amine (E)-2-butenedioate(1:3); mp.≧145° C. (compound 149).

In a similar manner there were also prepared:

N-[1-(2-aminoethyl)-3-pyrrolidinyl]-1-(4-thiazolylmethyl)-1H-benzimidazol-2-amine; decomposition > 80° C. (compound 150);

N-[1-(2-aminoethyl)-3-pyrrolidinyl]-3-(2-thienylmethyl)-3H-imidazo[4,5-b]pyridin-2-amine as a residue (compound 151);

N-[1-(2-aminoethyl)-3-pyrrolidinyl]-1-(2-thienylmethyl)-1H-benzimidazol-2-amine (E)-2-butenedioate(1:3); mp. 150° C. (compound 152);

N-[1-(2-aminoethyl)-3-pyrrolidinyl]-3-[(5-methyl-2-furanyl)methyl]-3H-imidazo-[4,5-b]pyridin-2-amine as a residue (compound 153); and N-[1-(2-aminoethyl)-3-pyrrolidinyl]-3-(4-thiazolylmethyl)-3H-imidazo [4,5-b]-pyridin-2-amine as a residue (compound 154).

Example 29

A mixture of 1.7 parts of 2-chloropyrimidine, 4.1 parts of N-[1-(2-aminoethyl)-3-pyrrolidinyl]-3-(4-thiazolylmethyl)-3H-imidazo[4,5-b]pyridin-2-amine, 2.1 parts of sodium carbonate and 108 parts of N,N-dimethylacetamide was stirred for 6 hours at 100° C. After cooling, the reaction mixture was poured into 600 parts of water and the product was extracted with dichloromethane. The extract was washed with water, dried, filtered and evaporated. The residue was converted into the (E)-2-butenedioate salt in 2-propanone and ethanol. The salt was filtered off, washed with 2-propanone and crystallized from a mixture of 2,2'-oxybispropane and methanol (1:1 by volume). The product was filtered off, washed with 2-propanone and dried in vacuo at 60° C., yielding 3.0 parts (32.1%) of N-[1-[2-(2-pyrimidinylamino)ethyl]-3-pyrrolidinyl]-3-(4-thiazolylmethyl)-3H-imidazo[4,5-b]pyridin-2-amine (E)-2-butenedioate(1:3),hemihydrate; mp. 161.7° C. (compound 155).

In a similar manner there were also prepared:

N-[1-[2-(2-pyrimidinylamino)ethyl]-3-pyrrolidinyl]-1-(4-thiazolylmethyl)-1H-benzimidazol-2-amine (E)-2-butenedioate(2:3),monohydrate; mp. 89.4° C. (compound 156);

1-(2-pyrazinylmethyl)-N-[1-[2-(2-pyrimidinylamino)ethyl]-3-pyrrolidinyl]-1H-benzimidazol-2-amine (E)-2-butenedioate(2:3),monohydrate; mp. 131.0° C. (compound 157);

N-[1-[2-(2-pyrimidinylamino)ethyl]-3-pyrrolidinyl]-3-(2-pyridinylmethyl)-3H-imidazo[4,5-b]pyridin-2-amine (E)-2-butenedioate(1:3); mp. 119.7° C. (compound 158);

N-[1-[2-(2-pyrimidinylamino)ethyl]-3-pyrrolidinyl]-1-(2-thienylmethyl)-1H-benzimidazol-2-amine ethanedioate(1:3),hemihydrate; mp. 174.4° C. (compound 159);

1-[(4-fluorophenyl)methyl]-N-[hexahydro-1-[2-(2-pyrimidinylamino)ethyl]-1H-azepin-4-yl]-1H-benzimidazol-2-amine ethanedioate(1:3); mp. 153.1° C. (compound 160); and 1-[(5-methyl-2-furanyl)methyl]-N-[hexahydro-1-[2-(2-pyrimidinylamino) ethyl]-1H-azepin-4-yl]-1H-benzimidazol-2-amine ethanedioate(1:3); mp. 139.8° C. (compound 161).

In a similar manner there are also prepared:

N-[hexahydro-1-[2-(2-pyridinylamino)ethyl]-1H-azepin-4-yl]-1-[(5-methyl-2-furanyl)methyl]-3H-imidazo[4,5-b]pyridin-2-amine (compound 162);

N-[hexahydro-1-[2-(2-pyrazinylamino)ethyl]-1H-azepin-4-yl]-1-[(5-methyl-2-furanyl)methyl]-3H-imidazo[4,5-b]pyridin-2-amine (compound 163);

N-[hexahydro-1-[2-[(6-chloro-3-pyridazinyl)amino]ethyl]-1H-azepin-4-yl]-1-[(5-methyl-2-furanyl)methyl]-3H-imidazo[4,5-b]pyridin-2-amine (compound 164);

Example 30

A mixture of 1.4 parts of 2-chloropyrimidine, 3.3 parts of N-[1-(2-aminoethyl)-3-pyrrolidinyl]-1-(2-pyridinylmethyl)-1H-benzimidazol-2-amine, 1.3 parts of sodium hydrogen carbonate and 60 parts of ethanol was stirred for 20 hours at reflux temperature. After filtration and evaporation of the filtrate, the residue was purified by column chromatography over silica gel using a mixture of trichloromethane, hexane, methanol and ammonium hydroxide (75:20:4.5:0.5 by volume) as eluent. The pure fractions were collected and the eluent was evaporated. The residue was converted into the (E)-2-butenedioate salt in 2-propanol. The salt was filtered off and crystallized from 2-propanol, yielding, after drying overnight at 80° C., 2.3 parts (31.0%) of 1-(2-pyridinylmethyl)-N-[1-[2-(2pyrimidinylamino)ethyl]-3-pyrrolidinyl]-1H-benzimidazol-2-amine (E)-2-butenedioate(2:3),2-propanolate(2:1); mp. 134.8° C. (compound 165).

In a similar manner there were also prepared:

1-[(4-fluorophenyl)methyl]-N-[1-[2-(2-pyrimidinylamino)ethyl]-3-pyrrolidinyl]-1H-benzimidazol-2-amine; mp. 164.1° C. (compound 166); and N-[1-[2-(2-pyrimidinylamino)ethyl]-3-pyrrolidinyl]-3-(2-thienylmethyl)-3H-imidazo[4,5-b]pyridin-2-amine (E)-2-butenedioate(1:1); mp. 178.2° C. (compound 167).

Example 31

A mixture of 12.8 parts of 2-bromothiazole, 22 parts of N-[1-(2-amino ethyl)-3-pyrrolidinyl]-1-[(4-fluorophenyl)methyl]-1H-benzimidazol-2-amine and 250 parts of pyridine was stirred and refluxed for 6 hours. After cooling, 12.8 parts of 2-bromothiazole were added and stirring was continued overnight at reflux temperature. The mixture was cooled and evaporated. The residue was taken up three times in methylbenzene and the latter was evaporated each time. The residue was purified by column chromatography over silica gel using a mixture of trichloromethane, hexane, methanol and ammonium hydroxide (45:45:10:1 by volume) as eluent. The pure and the less pure fractions were collected and the eluent was evaporated. The residue was purified by column chromatography (HPLC) over silica gel using a mixture of trichloromethane, methanol and methanol, saturated with ammonia, (96:3:1 by volume) as eluent.

The pure fractions were collected and the eluent was evaporated. The residue was crystallized from a mixture of 2,2'-oxybispropane and 2-propanone. The product was filtered off and dried, yielding 2.0 parts (7.3%) of 1-[(4-fluorophenyl)methyl]-N-[1-[2-(2-thiazolylamino)ethyl]-3-pyrrolidinyl]-1H-benzimidazol-2-amine; mp. 127.1° C. (compound 168).

Example 32

To a stirred mixture of 1 part of a sodium hydride dispersion 50% and 94 parts of N,N-dimethylformamide is added dropwise a solution of 5.5 parts of hexahydro-4-[[3-[(5-methyl-2-furanyl)methyl]-3H-imidazo[4,5-b]pyridin-2-yl]amino]-1H-azepine-1-ethanol in N,N-dimethylformamide. Upon complete addition, stirring is continued for 15 minutes at room temperature. 1.9 Parts of 2-chloropyrimidine are added portionwise and upon completion, stirring is continued for 2 hours at room temperature. The reaction mixture is decomposed with water and the product is extracted with dichloromethane. The extract is dried, filtered and evaporated. The residue is purified by column chromatography over silica gel using a mixture of trichloromethane and methanol (95:5 by volume) as eluent. The pure fractions are collected and the eluent was evaporated. The residue is converted into the ethanedioate salt in ethanol. The salt is filtered off and dried, yielding 3.4 parts (34.8%) of N-[hexahydro-1-[2-(2-pyrimidinyloxy)ethyl]-1H-azepin-4-yl]-3-[(5-methyl-2-furanyl)methyl]-3H-imidazo[4,5-b]pyridin-2-amine (compound 169).

In a similar manner there is also prepared:

N-[hexahydro-1-[2-(2-thiazolyloxy)ethyl]-1H-azepin-4-yl]-3-[(5-methyl-2-furanyl)methyl]-3H-imidazo[4,5-b]pyridin-2-amine (compound 170).

Example 33

To a stirred mixture of 4.2 parts of N,N-methyltetraylbis[cyclohexanamine] and 90 parts of tetrahydrofuran were added 10.6 parts of carbon disulfide. After stirring for 10 minutes, a solution of 6 parts of N-[1-(2-aminoethyl)-3-pyrrolidinyl]-3-[(5-methyl-2-furanyl)methyl]-3H-imidazo-[4,5-b]pyridin-2-amine in 36 parts of tetrahydrofuran was added dropwise to the thus obtained mixture (exothermic reaction, the temperature rose to 26° C.). Upon complete addition, stirring was continued for 30 minutes at room temperature. The reaction mixture was evaporated and the residue was taken up in 240 parts of acetonitrile. The precipitate was filtered off and the filtrate was evaporated, yielding 6.9 parts (100%) of N-[1-(2-isothiocyanatoethyl)-3-pyrrolidinyl]-3-[(5-methyl-2-furanyl)methyl]-3H-imidazo[4,5-b]pyridin-2-amine as a residue (compound 171).

In a similar manner there were also prepared:

1-[(4-fluorophenyl)methyl]-N-[1-(2-isothiocyanatoethyl)-3-pyrrolidinyl]-1H-benzimidazol-2-amine as an oily residue (compound 172);

N-[1-(2-isothiocyanatoethyl)-3-pyrrolidinyl]-1-(4-thiazolylmethyl)-1H-benzimidazol-2-amine as a residue (compound 173);

N-[1-(2-isothiocyanatoethyl)-3-pyrrolidinyl]-3-(2-thienylmethyl)-3H-imidazo[4,5-b]pyridin-2-amine as a residue (compound 174);

N-[1-(2-isothiocyanatoethyl)-3-pyrrolidinyl]-1-(2-thienylmethyl)-1H-benzimidazol-2-amine as an oily residue (compound 175); and N-[1-(2-isothiocyanatoethyl)-3-pyrrolidinyl]-3-(4-thiazolylmethyl)-3H-imidazo-[4,5-b]pyridin-2-amine as a residue (compound 176).

Example 34

A mixture of 2.8 parts of 3,4-pyridinediamine, 10.7 parts of 1-[(4-fluorophenyl)methyl]-N-[1-(2-isothiocyanatoethyl)-3-pyrrolidinyl]-1H-benzimidazol-2-amine and 90 parts of tetrahydrofuran was stirred and refluxed for 7 hours. The precipitated product was filtered off while hot, washed with a small amount of tetrahydrofuran and dried, yielding 6.5 parts (51%) of N-(4-amino-3-pyridinyl)-N'-[2-[3-[[1-[(4-fluorophenyl)methyl]-1H-benzimidazol-2-yl]amino]-1-pyrrolidinyl]ethyl]thiourea; mp. 225° C. (compound 177).

In a similar manner there were also prepared:

N-(4-amino-3-pyridinyl)-N'-[2-[3-[[1-(4-thiazolylmethyl)-1H-benzimidazol-2-yl]amino]-1-pyrrolidinyl]ethyl]thiourea; mp. 220.0° C. (compound 178);

N-(4-amino-3-pyridinyl)-N'-[2-[3-[[3-(2-thienylmethyl)-3H-imidazo[4,5-b]pyridin-2-yl]amino]-1-pyrrolidinyl]ethyl]thiourea; mp. 172.2° C. (compound 179);

N-(4-amino-3-pyridinyl)-N'-[2-[3-[[1-(2-thienylmethyl)-1H-benzimidazol-2-yl]amino]-1-pyrrolidinyl]-ethyl]-thiourea as a residue (compound 180);

N-(4-amino-3-pyridinyl)-N'-[2-[3-[[3-[(5-methyl-2-furanyl)methyl]-3H-imidazo-[4,5-b]pyridin-2-yl]amino]-1-pyrrolidinyl]ethyl]thiourea as a residue (compound 181); and N-(4-amino-3-pyridinyl)-N'-[2-[3-[[3-(4-thiazolylmethyl)-3H-imidazo[4,5-b]-pyridin-2-yl]amino]-1-pyrrolidinyl]ethyl]thiourea as a residue (compound 182).

Example 35

A mixture of 10.5 parts of N-(4-amino-3-pyridinyl)-N'-[2-[3-[[3-(4-thiazolylmethyl)-3H-imidazo[4,5-b]-pyridin-2-yl]amino]-1-pyrrolidinyl]ethyl]thiourea, 11.5 parts of mercury(II) oxide, 0.1 parts of sulfur and 168 parts of methanol, saturated with ammonia was stirred for 30 minutes at reflux temperature. The reaction mixture was filtered while hot over diatomaceous earth and washed with warm methanol. The filtrate was evaporated and the residue was purified by column chromatography over silica gel using a mixture of trichloromethane, methanol and ammonium hydroxide (90:9:1 by volume) as eluent. The pure fractions were collected and the eluent was evaporated. The residue was converted into the (E)-2-butenedioate salt in 160 parts of 2-propanone and 160 parts of ethanol. The salt was filtered off and dried, yielding 4.1 parts (23.1%) of N-[1-[2-[(1H-imidazo[4,5-c]pyridin-2-yl)amino]ethyl]-3-pyrrolidinyl]-3-(4-thiazolylmethyl)-3H-imidazo[4,5-b]pyridin-2-amine (E)-2-butenedioate(1:3), dihydrate; mp. 157.2° C. (compound 183).

In a similar manner there were also prepared:

N-[2-[3-[[1-[(4-fluorophenyl)methyl]-1H-benzimidazol-2-yl]amino]-1-pyrrolidinyl]ethyl]-1H-imidazo[4,5-c]pyridin-2-amine monohydrate; mp. 140.1° C. (compound 184);

N-[2-[3-[[1-(4-thiazolylmethyl)-1H-benzimidazol-2-yl]amino]-1-pyrrolidinyl]ethyl]-1H-imidazo[4,5-c]pyridin-2-amine ethanedioate(1:4); mp. 173.6° C. (compound 185);

N-[2-[3-[[1-(2-thienylmethyl)-1H-benzimidazol-2-yl]amino]-1-pyrrolidinyl]ethyl]-1H-imidazo-[4,5-c]pyridin-2-amine ethanedioate(1:4); mp. 180.9° C. (dec.) (compound 186); and N-[1-[2-[(1H-imidazo[4,5-c]pyridin-2-yl)amino]ethyl]-3-pyrrolidinyl]-3-[(5-methyl-2-furanyl)methyl]-3H-imidazo[4,5-b]pyridin-2-amine ethanedioate(2:5), dihydrate; mp. 88.7° C. (compound 187).

Example 36

A mixture of 0.9 parts of isocyanatomethane, 5.3 parts of N-[1-(2-aminoethyl)-3-pyrrolidinyl]-1-[(4-fluorophenyl)methyl]-1H-benzimidazol-2-amine and 63 parts of tetrahydrofuran was stirred for 1.5 hour at room temperature using a CaCl$_2$-tube. Another portion of 0.9 parts of isocyanatomethane was added and stirring was continued for 1.5 hour at room temperature. The precipitated product was filtered off, washed with tetrahydrofuran and dried in vacuo at room temperature, yielding 5.0 parts (81%) of N-[2-[3-[[1-[(4-fluorophenyl)methyl]-1H-benzimidazol-2-yl]amino]-1-pyrrolidinyl]ethyl]-N'-methylurea; mp. 161.1° C. (compound 188).

In a similar manner there was also prepared:
N-[2-[3-[[1-[(4-fluorophenyl)methyl]-1H-benzimidazol-2-yl]amino]-1-pyrrolidinyl]ethyl]-N'-methylthiourea; mp. 169.0° C. (compound 189).

Example 37

To a stirred mixture of 1.12 parts of 3-furancarboxylic acid, 2.02 parts of N,N-diethylethanamine and 195 parts of dichloromethane are added 2.6 parts of 2-chloro-1-methylpyridinium iodide at room temperature. After stirring for 1 hour, 3.3 parts of N-[1-(2-aminoethyl)hexahydro-1H-azepin-4-yl]-3-[(5-methyl-2-furanyl)methyl]-3H-imidazo[4,5-b]pyridin-2-amine are added and stirred overnight at room temperature. The mixture is poured into water and the layers are separated. The organic layer is dried, filtered and evaporated. The residue is purified by column chromatography over silica gel using a mixture of trichloromethane and methanol (96:4 by volume) as eluent. The pure fractions are collected and the eluent is evaporated, yielding 2.19 parts (36.1%) of N-[2-[hexahydro-4-[[3-[(5-methyl-2-furanyl)methyl]-3H-imidazo[4,5-b]pyridin-2-yl]amino]-1H-azepin-4-yl]ethyl]-3-furancarboxamide as a residue (compound 190).

In a similar manner there are also prepared:
N-[2-[hexahydro-4-[[3-[(5-methyl-2-furanyl)methyl]-3H-imidazo[4,5-b]pyridin-2-yl]amino]-1H-azepin-4-yl]ethyl]-2-thiazolecarboxamide (compound 191); and
2-amino-N-[2-[hexahydro-4-[[3-[(5-methyl-2-furanyl)methyl]-3H-imidazo[4,5-b]pyridin-2-yl]amino]-1H-azepin-4-yl]ethyl]benzamide (compound 192).

Example 38

A mixture of 6 parts of 3-[(5-methyl-2-furanyl)methyl]-N-(3-pyrrolidinyl)-3H-imidazo[4,5-b]pyridin-2-amine monohydrochloride, 2 parts of poly(oxymethylene), 1 part of a solution of thiophene in methanol 4%, 160 parts of methanol and 6 parts of potassium acetate was hydrogenated at normal pressure and at room temperature with 2 parts of palladium-on-charcoal catalyst 10%. After the calculated amount of hydrogen was taken up, the catalyst was filtered off and the filtrate was evaporated. The residue was taken up in water and a small amount of concentrated ammonium hydroxide was added. The product was extracted twice with trichloromethane. The combined extracts were washed with water, dried, filtered and evaporated. The oily residue was converted into the (E)-2-butenedioate salt in 320 parts of 2-propanone. The salt was filtered off, washed with 2-propanone and crystallized from 2-propanol. The product was filtered off and dried in vacuo at 60° C., yielding 1.5 parts (15.3%) of 3-[(5-methyl-2-furanyl)methyl]-N-(1-methyl-3-pyrrolidinyl)-3H-imidazo[4,5-b]-pyridin-2-amine (E)-2-butenedioate(1:2); mp. 168.6° C. (compound 193).

In a similar manner there were also prepared:
N-(1-methyl-3-pyrrolidinyl)-3-(2-pyridinylmethyl)-3H-imidazo[4,5-b]pyridin-2-amine ethanedioate(1:2); mp. 163.6° C. (compound 194); and
N-(1-methyl-3-pyrrolidinyl)-3-(4-thiazolylmethyl)-3H-imidazo[4,5-b]pyridin-2-amine ethanedioate(1:2); mp. 196.3° C. (compound 195).

Example 39

A mixture of 3.1 parts of 3-(2-furanylmethyl)-N-(hexahydro-1H-azepin-4-yl)-3H-imidazo[4,5-b]pyridin-2-amine, 2 parts of poly(oxymethylene), 1 part of a solution of thiophene in methanol 4% and 120 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the ethanedioate salt in 2-propanol. The salt was filtered off and crystallized from methanol. The product was filtered off and dried, yielding 2.2 parts (43.5%) of 3-(2-furanylmethyl)-N-(hexahydro-1-methyl-1H-azepin-4-yl)-3H-imidazo[4,5-b]-pyridin-2-amine ethanedioate(1:2); mp. 183.5° C. (compound 196).

In a similar manner there were also prepared:
1-[(4-fluorophenyl)methyl]-N-(hexahydro-1-methyl-1H-azepin-4-yl)-1H-benzimidazol-2-amine (E)-2-butenedioate(1:2); mp. 209.2° C. (compound 197);
N-(hexahydro-1-methyl-1H-azepin-4-yl)-1-[(5-methyl-2-furanyl)methyl]-1H-benzimidazol-2-amine ethanedioate(1:2); mp. 207.6° C. (compound 198);
9-[(4-fluorophenyl)methyl]-N-(hexahydro-1-methyl-1H-azepin-4-yl)-9H-purin-8-amine; mp. 117.2° C. (compound 199);
1-[(4-fluorophenyl)methyl]-N-(hexahydro-1-methyl-1H-azepin-4-yl)-1H-imidazo[4,5-c]pyridin-2-amine; mp. 170.1° C. (compound 200);
N-[hexahydro-1-(1-methylethyl)-1H-azepin-4-yl]-3-[(5-methyl-2-furanyl)methyl]-3H-imidazo[4,5-b]pyridin-2-amine (E)-2-butenedioate(1:2); mp. 110.1° C. (compound 201);
N-(hexahydro-1-methyl-1H-azepin-4-yl)-3-[(5-methyl-2-furanyl)methyl]-3H-imidazo[4,5-c]pyridin-2-amine; mp. 107.7° C. (compound 202);
1-[(4-fluorophenyl)methyl]-N-(1-methyl-3-pyrrolidinyl)-1H-benzimidazol-2-amine; mp. 138.7° C. (compound 203);
1-[(4-fluorophenyl)methyl]-N-[1-(1-methylethyl)-3-pyrrolidinyl]-1H-benzimidazol-2-amine; mp. 135.5° C. (compound 204); and
N-(1-methyl-3-pyrrolidinyl)-1-(2-thienylmethyl)-1H-benzimidazol-2-amine ethanedioate(1:2); mp. 225.2° C. (compound 205).

Example 40

A mixture of 6 parts of N-(hexahydro-1H-azepin-4-yl)-3-[(5-methyl-2-furanyl)methyl]-3H-imidazo[4,5-b]-pyridin-2-amine ethanedioate(1:2) and 64 parts of methanol, saturated with ammonia was stirred for 5 minutes at reflux temperature. After cooling, the precipitate was filtered off and the filtrate was evaporated. A mixture of the residue, 5 parts of cyclohexanone, 1 part of a solution of thiophene in methanol 4% and 120 parts of methanol was hydrogenated at normal pressure and at room temperature with 1 part of palladium-on-charcoal catalyst 10%. After the calculated amount of hydrogen was taken up, the catalyst was filtered off and the filtrate was evaporated. The residue was converted into the ethanedioate salt in a small amount of 2-propanone and ethanol. After cooling, the salt was filtered off and crystallized from ethanol. The product was filtered off and dried, yielding 2 parts (23.9%) of N-(1-cyclohexyl-hexahydro-1H-azepin-4-yl)-3-[(5-methyl-2-furanyl)methyl]-3H-imidazo[4,5-b]pyridin-2-amine ethanedioate(1:2), hemihydrate; mp. 136.1° C. (compound 206).

In a similar manner there was also prepared:
N-(hexahydro-1-methyl-1H-azepin-4-yl)-3-[(5-methyl-2-furanyl)methyl]-3H-imidazo[4,5-b]pyridin-2-amine ethanedioate(1:2); mp. 174.2° C. (compound 207).

Example 41

A mixture of 1.3 parts of 2-ethenylpyridine, 6.2 parts of 1-[(4-fluorophenyl)methyl]-N-(3-pyrrolidinyl)-1H-benzimidazol-2-amine and 56 parts of 1-butanol was stirred and refluxed for 3 hours. Another 3.5 parts of 2-ethenylpyridine were added and stirring at reflux was continued for 3.5 hours. The reaction mixture was evaporated. The residue was purified by column chromatography over silica gel using a mixture of trichloromethane and methanol (90:9:1 by volume) as eluent. The pure fractions were collected and the eluent was evaporated. The residue was converted into the ethanedioate salt in 2-propanone. The salt was filtered off and dried in vacuo at 60° C., yielding 8.0 parts (54%) of 1-[(4-fluorophenyl)methyl]-N-[1-[2-(2-pyridinyl)ethyl]-3-pyrrolidinyl]-1H-benzimidazol-2-amine ethanedioate(2:7); mp. 194.0° C. (compound 208).

Example 42

Gazeous oxirane was bubbled through a stirred mixture of 6.2 parts of 1-[(4-fluorophenyl)methyl]-N-(3-pyrrolidinyl)-1H-benzimidazol-2-amine and 120 parts of methanol for 1.50 hour at 30° C. The reaction mixture was evaporated. The residue was purified by column chromatography over silica gel using a mixture of trichloromethane, methanol and ammonium hydroxide (90:9:1 by volume) as eluent. The pure fractions were collected and the eluent was evaporated. The residue was converted into the hydrochloride salt in 2-propanol. The salt was filtered off, washed with 2-propanone and dried in vacuo at 80° C., yielding 3.8 parts (44%) of 3-[[1-[(4-fluorophenyl)methyl]-1H-benzimidazol-2-yl]amino]-1-pyrrolidineethanol dihydrochloride; mp. 230.3° C. (compound 209).

In a similar manner there is also prepared:
hexahydro-4-[[3-[(5-methyl-2-furanyl)methyl]-3H-imidazo[4,5-b]pyridin-2-yl]amino]-α-(phenoxymethyl)-1H-azepine-1-ethanol (compound 210).

Example 43

A mixture of 11.3 parts of N-(hexahydro-1H-azepin-4-yl)-1-[(5-methyl-2-furanyl)methyl]-1H-benzimidazol-2-amine (E)-2-butenedioate(2:3), hemihydrate, 10.6 parts of sodium carbonate and 120 parts of methanol was stirred for 30 minutes at reflux temperature. After cooling to 30° C., gaseous oxirane was bubbled during 2 hours through the mixture. The reaction mixture was evaporated and the residue was stirred in dichloromethane. The precipitate was filtered off over diatomaceous earth and the filtrate was evaporated. The residue was purified by column chromatography over silica gel using a mixture of trichloromethane, methanol and ammonium hydroxide (90:9:1 by volume) as eluent. The pure fractions were collected and the eluent was evaporated. The residue was converted into the ethanedioate salt in 2-propanone. The salt was filtered off and crystallized from a mixture of 2-propanone and ethanol. The product was filtered off and dried, yielding 0.7 parts (6.3%) of hexahydro-4-[[1-[(5-methyl-2-furanyl)methyl]-1H-benzimidazol-2-yl]amino]-1H-azepine-1-ethanol ethanedioate(1:2); mp. 155.8° C. (compound 211).

Example 44

5 Parts of N-(3-pyrrolidinyl)-1-(2-thienylmethyl)-1H-benzimidazol-2-amine were converted into the ethanedioate salt in a mixture of methanol and 2-propanone. The salt was filtered off, washed with 2-propanone and the product was boiled in 160 parts of ethanol. The mixture was allowed to cool while stirring. The precipitated product was filtered off and dried, yielding 2.8 parts (42.4%) of N-(3-pyrrolidinyl)-1-(2-thienylmethyl)-1H-benzimidazol-2-amine ethanedioate(1:1); mp. 222.5° C. (compound 212).

Example 45

To a stirred and heated (50° C.) mixture of 6.4 parts of lithium tetrahydroaluminate and 450 parts of tetrahydrofuran were added portionwise 23.5 parts of ethyl 4-(1H-benzimidazol-2-ylamino)hexahydro-1H-azepine-1-carboxylate under nitrogen atmosphere. Upon complete addition, stirring was continued for 2 hours at reflux temperature. The reaction mixture was decomposed with ethyl acetate, 30 parts of a sodium hydroxide solution and 30 parts of water. The whole was filtered over diatomaceous earth and the filtrate was evaporated. The residue was crystallized from acetonitrile. The product was filtered off and dried, yielding 10.5 parts (55.0%) of N-(hexahydro-1-methyl-1H-azepin-4-yl)-1H-benzimidazol-2-amine; mp. 168.3° C. (compound 213).

In a similar manner there were also prepared:

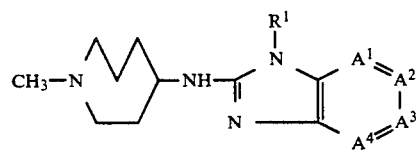

| Comp. No. | $R^1$ | $A^1=A^2-A^3=A^4$ | base/salt | mp (°C.) |
|---|---|---|---|---|
| 214 | 4-F—$C_6H_4$—$CH_2$— | CH=CH—C(OCH$_3$)=CH | (E)-2-butenedioate(1:2) | 181.6 |

-continued

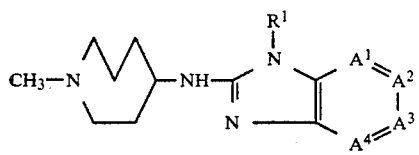

| Comp. No. | R¹ | A¹=A²—A³=A⁴ | base/salt | mp (°C.) |
|---|---|---|---|---|
| 215 | 4-F—C₆H₄—CH₂— | CH=C(OCH₃)—CH=CH | base | 165.6 |
| 216 | C₆H₅—CH₂— | CH=CH—CH=CH | base | 100.4 |
| 217 | 4-CH₃—C₆H₄—CH₂— | CH=CH—CH=CH | (E)-2-butenedioate(1:2) | 225.5 |
| 218 | 4-F—C₆H₄—CH₂— | CH=CH—CH=CH | (E)-2-butenedioate(1:2) | 208.8 |
| 219 | 4-F—C₆H₄—CH₂— | CH=CH—C(CH₃)=CH | (E)-2-butenedioate(1:2) | 214.5 |
| 220 | C₂H₅— | CH=CH—CH=CH | 2 HCl ½ H₂O | 219.4 |
| 221 | 2-thienylmethyl | CH=CH—CH=CH | (E)-2-butenedioate(2:3) | 158.6 |
| 222 | 4-F—C₆H₄—CH₂— | CH=C(F)—C(F)=CH | (E)-2-butenedioate(1:2) | 194.9 |
| 223 | (4-F—C₆H₄)₂CH— | CH=CH—CH=CH | 2 (COOH)₂ | 170.3 |
| 224 | 2-pyridinylmethyl | CH=CH—CH=CH | | |
| 225 | 2-pyrazinylmethyl | CH=CH—CH=CH | | |
| 226 | 4-thiazolylmethyl | CH=CH—CH=CH | | |
| 227 | (5-methyl 1H-imidazol-4-yl)methyl | CH=CH—CH=CH | | |
| 228 | (5-methyl-2-furanyl)methyl | CH=CH—CH=CH | | |

C) Pharmacological Examples

The useful anti-histaminic properties of the compounds of formula (I) which can be used as the active ingredient in the formulations according to the present invention can be demonstrated by the following test procedure.

Example 46

Protection of rats from compound 48/80-induced lethality

Compound 48/80, a mixture of oligomers obtained by condensation of 4-methoxy-N-methylbenzeneethanamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test compounds. Male rats of an inbred Wistar strain, weighing 240-260 g were used in the experiment. After overnight starvation the rats were transferred to conditioned laboratories (temp.=21°±1° C., relative humidity=65±5%). The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration. The ED₅₀-values of the compounds of formula (I) are listed in table 1. Said ED₅₀-values are the values in mg/kg body weight at which the tested compounds protect 50% of the tested animals against compound 48/80-induced lethality.

TABLE 1

| No. | compound 48/80 lethality test in rats-ED₅₀ in mg/kg body weight |
|---|---|
| 49 | 0.04 |
| 61 | 0.08 |
| 68 | 0.04 |
| 94 | 0.04 |
| 95 | 0.04 |
| 96 | 0.04 |
| 99 | 0.04 |
| 102 | 0.04 |
| 109 | 0.04 |
| 125 | 0.08 |
| 166 | 0.08 |
| 168 | 0.08 |
| 186 | 0.01 |
| 187 | 0.04 |
| 188 | 0.01 |
| 207 | 0.01 |
| 196 | 0.02 |
| 198 | 0.04 |
| 204 | 0.04 |
| 211 | 0.04 |

D) Composition Examples

The following formulations exemplify typical pharmaceutical compositions in dosage unit form suitable for systemic administration to animal and human subjects in accordance with the instant invention.

"Active ingredient" (A.I.) as used throughout these examples relates to a compound of formula (I) or a pharmaceutically acceptable acid addition salt thereof.

Example 47: Oral Drops 500 g of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg of the A.I. per ml. The resulting solution was filled into suitable containers.

Example 48: Oral Solution 9 g of methyl 4-hydroxybenzoate and 1 g of propyl 4-hydroxybenzoate were dissolved in 4 l of boiling purified water. In 3 l of this solution were dissolved first 10 g of 2,3-dihydroxybutanedioic acid and thereafter 20 g of the A.I. The latter solution was combined with the remaining part of the former solution and 12 l 1,2,3-propanetriol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 20 mg of the active ingredient per teaspoonful (5 ml). The resulting solution was filled in suitable containers.

Example 49: Capsules 20 g of the A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelating capsules, comprising each 20 mg of the active ingredient.

Example 50: Film-Coated Tablets

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90 ®) in about 200 ml of water. The wet powder mixture was sieved, dried and sieved again. Then there was added 100 g microcrystalline cellulose (Avicel ®) and 15 g hydrogenated vegetable oil (Sterotex ®). The whole was mixed well and compressed into tablets, giving 10.000 tablets, each containing 10 mg of the active ingredient.

Coating

To a solution of 10 g methyl cellulose (Methocel 60 HG ®) in 75 ml of denaturated ethanol there was added a solution of 5 g of ethyl cellulose (Ethocel 22 cps ®) in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated colour suspension (Opaspray K-1-2109 ®) and the whole was homogenated. The tablet cores were coated with the thus obtained mixture in a coating apparatus.

Example 51: Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg A.I. per ml. The solution was sterilized by filtration (U.S.P. XVII p. 811) and filled in sterile containers.

Example 52: Suppositories 3 g A.I. was dissolved in a solution of 3 g 2,3-dihydroxybutanedioic acid in 25 ml polyethylene glycol 400. 12 g Surfactant (SPAN ®) and triglycerides (Witepsol 555 ®) q.s. ad 300 g were molten together. The latter mixture was mixed well with the former solution. The thus obtained mixture was poured into moulds at a temperature of 37°-38° C. to form 100 suppositories each containing 30 mg of the active ingredient.

What is claimed is:

1. A compound of the formula:

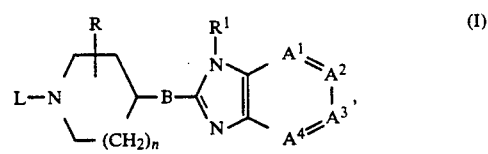

a pharmaceutically acceptable acid addition salt or a stereochemically isomeric form thereof, wherein:
—$A^1$=$A^2$—$A^3$=$A^4$— represents a bivalent radical of the formula:

| | |
|---|---|
| —CH=CH—CH=CH—, | (a-1) |
| —N=CH—CH=CH—, | (a-2) |
| —CH=N—CH=CH—, | (a-3) |
| —CH=CH—N=CH—, | (a-4) |
| —CH=CH—CH=N—, | (a-5) |
| —N=CH—N=CH—, or | (a-6) |
| —CH=N—CH=N—, | (a-7) | wherein one or two hydrogen atoms in said radicals (a-1)-(a-7) may, each independently from each other, be replaced by halo, $C_{1-6}$alkyl, $C_{1-6}$alkyloxy, trifluoromethyl, or hydroxy;

$R^1$ represents hydrogen, $C_{1-10}$alkyl, $C_{3-6}$cycloalkyl, $Ar^1$ or $C_{1-6}$alkyl substituted with one or two $Ar^1$ radicals;

B represents $NR^2$, $CH_2$, O, S, SO, or $SO_2$, wherein $R^2$ represents hydrogen, $C_{1-6}$alkyl, $C_{3-6}$cycloalkyl, $C_{1-6}$alkylcarbonyl, $C_{1-6}$alkyloxycarbonyl, or $Ar^2$-$C_{1-6}$alkyl;

R represents hydrogen or $C_{1-6}$alkyl;

n represents 0 or 2; and

L represents a group of the formula:

| | |
|---|---|
| -Alk-$R^3$; | (b-1) |
| -Alk-Y—$R^4$; or | (B-2) |
| -Alk-$Z^1$—(C=X)—$Z^2$—$R^5$, | (b-3) | wherein:

$R^3$, $R^4$, and $R^5$ individually represent Het;

Y represents O, S, or $NR^7$, wherein $R^7$ represents hydrogen, $C_{1-6}$alkyl, $C_{1-6}$alkylcarbonyl, or $Ar^1$-carbonyl;

$Z^1$ and $Z^2$ each independently represent O, S, $NR^8$, or a direct bond, wherein $R^8$ represents hydrogen or $C_{1-6}$alkyl;

X represents O, S or $NR^9$, wherein $R^9$ represents hydrogen, $C_{1-6}$alkyl, or cyano; and each Alk independently represents $C_{1-6}$alkanediyl;

wherein the foregoing:

Het represents a member selected from the group consisting of pyridinyl which is optionally substituted with one or two substituents each independently selected from halo, amino, mono- and di(C$_{1-6}$alkyl)amino, Ar$^2$C$_{1-6}$alkylamino, nitro, cyano, aminocarbonyl, C$_{1-6}$alkyl, C$_{1-6}$alkyloxy, C$_{1-6}$alkylthio, C$_{1-6}$alkyloxycarbonyl, hydroxy, C$_{1-6}$alkylcarbonyloxy, Ar$^2$C$_{1-6}$alkyl and carboxyl; pyridinyloxide optionally substituted with nitro; pyrimidinyl which is optionally substituted with one or two substituents each independently selected from the group consisting of halo, amino, hydroxy, C$_{1-6}$alkyl, C$_{1-6}$alkyloxy, C$_{1-6}$alkylthio, and Ar$^2$C$_{1-6}$alkyl; pyridazinyl which is optionally substituted with C$_{1-6}$alkyl or halo; pyrazinyl which is optionally substituted with, halo, amino or C$_{1-6}$alkyl; thienyl which is optionally substituted with halo or C$_{1-6}$alkyl; furanyl which is optionally substituted with halo or C$_{1-6}$alkyl; pyrrolyl which is optionally substituted with C$_{1-6}$alkyl; thiazolyl which is optionally substituted with C$_{1-6}$alkyl, C$_{1-6}$alkyloxycarbonyl, Ar$^2$ or Ar$^2$C$_{1-6}$alkyl; imidazolyl which is optionally substituted with one or two substituents each independently selected from C$_{1-6}$alkyl and nitro; tetrazolyl which is optionally substituted with C$_{1-6}$alkyl; 1,3,4-thiadiazolyl which is optionally substituted with C$_{1-6}$alkyl; 5,6-dihydro-4H-1,3-thiazin-2-yl which is optionally substituted with C$_{1-6}$alkyl; 4,5-dihydrothiazolyl which is optionally substituted with C$_{1-6}$alkyl; oxazolyl which is optionally substituted with C$_{1-6}$alkyl; 4,5-dihydro-5-oxo-1H-tetrazolyl which is optionally substituted with C$_{1-6}$alkyl; 1,4-dihydro-2,4-dioxo-3(2H)-pyrimidinyl being optionally substituted with C$_{1-6}$alkyl; 4,5-dihydro-4-oxo-2-pyrimidinyl; 2-oxo-3-oxazolidinyl; dioxanyl being optionally substituted with C$_{1-6}$alkyl; morpholinyl; thiomorpholinyl; and piperidinyl;

Ar$^1$ represents a member selected from the group consisting of phenyl which may optionally be substituted with 1, 2, or 3 substituents each independently selected from the group consisting of halo, hydroxy, nitro, cyano, trifluoromethyl, C$_{1-6}$alkyl, C$_{1-6}$alkyloxy, C$_{1-6}$alkylthio, mercapto, amino, mono- and di(C$_{1-6}$alkyl)amino, carboxyl, C$_{1-6}$alkyloxycarbonyl, and C$_{1-6}$alkylcarbonyl; thienyl; halothienyl; furanyl; C$_{1-6}$alkyl substituted furanyl; pyridinyl; pyrimidinyl; pyrazinyl; thiazolyl; and imidazolyl optionally substituted with C$_{1-6}$alkyl; and Ar$^2$ represents a member selected from the group consisting of phenyl which may optionally be substituted with 1, 2, or 3 substituents each independently selected from the group consisting of halo, hydroxy, nitro, cyano, trifluoromethyl, C$_{1-6}$alkyl, C$_{1-6}$alkyloxy, C$_{1-6}$alkylthio, mercapto, amino, mono- and di(C$_{1-6}$alkyl)amino, carboxyl, C$_{1-6}$alkyloxycarbonyl, and C$_{1-6}$alkylcarbonyl.

2. A compound according to claim 1 wherein n=2.
3. A compound according to claim 1 wherein n=0.
4. A compound according to claim 1 wherein R represents hydrogen, R$^1$ represents C$_{1-6}$alkyl substituted with one Ar$^1$, and B represents NH or CH$_2$.
5. A compound according to claim 4 wherein B represents NH.
6. A compound according to claim 1 wherein said compound is a member selected from the group consisting of:

1-ethyl-4-[2-[hexahydro-4-[[3-[(5-methyl-2-furanyl)methyl]-3H-imidazo[4,5-b]pyridin-2-yl]amino]-1H-azepin-1-yl]ethyl]-1,4-dihydro-5H-tetrazol-5-one;

1-[(4-fluorophenyl)methyl]-N-[hexahydro-1-[2-(pyrimidinylamino)ethyl]-1H-azepin-4-yl]-1H-benzimidazol-2-amine;

1-[(4-fluorophenyl)methyl]-N-[1-[2-(2-pyrimidinylamino)ethyl]-3-pyrrolidinyl]-1H-benzimidazol-2-amine;

1-[(4-fluorophenyl)methyl]-N-[1-[2-(2-thiazolylamino)ethyl]-3-pyrrolidinyl]-1H-benzimidazol-2-amine; and 1-[(4-fluorophenyl)methyl]-N-[1-[2-(2-pyridinyl)ethyl]-3-pyrrolidinyl]-1H-benzimidazol-2-amine.

7. An anti-allergic composition comprising one or more pharmaceutical carriers and as active ingredient a compound of the formula:

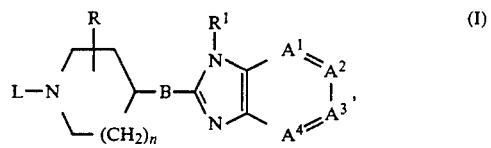

a pharmaceutically acceptable acid addition salt or a stereochemically isomeric form thereof, wherein:

—A$^1$=A$^2$—A$^3$=A$^4$— represents a bivalent radical of the formula:

| | |
|---|---|
| —CH=CH—CH=CH—, | (a-1) |
| —N=CH—CH=CH—, | (a-2) |
| —CH=N—CH=CH—, | (a-3) |
| —CH=CH—N=CH—, | (a-4) |
| —CH=CH—CH=N—, | (a-5) |
| —N=CH—N=CH—, or | (a-6) |
| —CH=N—CH=N—, | (a-7) | wherein one or two hydrogen atoms in said radicals (a-1)–(a-7) may, each independently from each other, be replaced by halo, C$_{1-6}$alkyl, C$_{1-6}$alkyloxy, trifluoromethyl, or hydroxy;

R$^1$ represents hydrogen, C$_{1-10}$alkyl, C$_{3-6}$cycloalkyl, Ar$^1$ or C$_{1-6}$alkyl substituted with one or two Ar$^1$ radicals;

B represents NR$^2$, CH$_2$, O, S, SO, or SO$_2$, wherein R$^2$ represents hydrogen, C$_{1-6}$alkyl, C$_{3-6}$cycloalkyl, C$_{1-6}$alkylcarbonyl, C$_{1-6}$alkyloxycarbonyl, or Ar$^2$-C$_{1-6}$alkyl;

R represents hydrogen or C$_{1-6}$alkyl;

n represents 0 or 2; and

L represents a group of the formula:

| | |
|---|---|
| -Alk-R$^3$; | (b-1) |
| -Alk-Y—R$^4$; or | (B-2) |
| -Alk-Z$^1$—(C=X)—Z$^2$—R$^5$, | (b-3) | wherein:

R$^3$, R$^4$, and R$^5$ individually represent Het;

Y represents O, S, or NR$^7$, wherein R$^7$ represents hydrogen, C$_{1-6}$alkyl, C$_{1-6}$alkylcarbonyl, or Ar$^1$-carbonyl;

$Z^1$ and $Z^2$ each independently represent O, S, $NR^8$, or a direct bond, wherein $R^8$ represents hydrogen or $C_{1-6}$alkyl;

X represents O, S or $NR^9$, wherein $R^9$ represents hydrogen, $C_{1-6}$alkyl, or cyano; and each Alk independently represents $C_{1-6}$alkanediyl; wherein in the foregoing:

Het represents a member selected from the group consisting of pyridinyl which is optionally substituted with one or two substituents each independently selected from halo, amino, mono- and di(C$_{1-6}$alkyl)amino, $Ar^2C_{1-6}$alkylamino, nitro, cyano, aminocarbonyl, $C_{1-6}$alkyl, $C_{1-6}$alkyloxy, $C_{1-6}$alkylthio, $C_{1-6}$alkyloxycarbonyl, hydroxy, $C_{1-6}$alkylcarbonyloxy, $Ar^2C_{1-6}$alkyl and carboxyl; pryidinyloxide optionally substituted with nitro; pyrimidinyl which is optionally substituted with one or two substituents each independently selected from the group consisting of halo, amino, hydroxy, $C_{1-6}$alkyl, $C_{1-6}$alkyloxy, $C_{1-6}$alkylthio, and $Ar^2C_{1-6}$alkyl; pyridazinyl which is optionally substituted with $C_{1-6}$alkyl or halo; pyrazinyl which is optionally substituted with, halo, amino or $C_{1-6}$alkyl; thienyl which is optionally substituted with halo or $C_{1-6}$alkyl; furanyl which is optionally substituted with halo or $C_{1-6}$alkyl; pyrrolyl which is optionally substituted with $C_{1-6}$alkyl; thiazolyl which is optionally substituted with $C_{1-6}$alkyl, $C_{1-6}$alkyloxycarbonyl, $Ar^2$ or $Ar^2C_{1-6}$alkyl; imidazolyl which is optionally substituted with one or two substituents each independently selected from $C_{1-6}$alkyl and nitro; tetrazolyl which is optionally substituted with $C_{1-6}$alkyl; 1,3,4-thiadiazolyl which is optionally substituted with $C_{1-6}$alkyl; 5,6-dihydro-4H-1,3-thiazin-2-yl which is optionally substituted with $C_{1-6}$alkyl; 4,5-dihydrothiazolyl which is optionally substituted with $C_{1-6}$alkyl; oxazolyl which is optionally substituted with $C_{1-6}$alkyl; 4,5-dihydro-5-oxo-1H-tetrazolyl which is optionally substituted with $C_{1-6}$alkyl; 1,4-dihydro-2,4-dioxo-3(2H)-pyrimidinyl being optionally substituted with $C_{1-6}$alkyl; 4,5-dihydro-4-oxo-2-pyrimidinyl; 2-oxo-3-oxazolidinyl; dioxanyl being optionally substituted with $C_{1-6}$alkyl; morpholinyl; thiomorpholinyl; and piperidinyl;

$Ar^1$ represents a member selected from the group consisting of phenyl which may optionally be substituted with 1, 2, or 3 substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl, and $C_{1-6}$alkylcarbonyl; thienyl; halothienyl; furanyl; $C_{1-6}$alkyl substituted furanyl; pyridinyl; pyrimidinyl; pyrazinyl; thiazolyl; and imidazolyl optionally substituted with $C_{1-6}$alkyl; and $Ar^2$ represents a member selected from the group consisting of phenyl which may optionally be substituted with 1, 2, or 3 substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl, and $C_{1-6}$alkylcarbonyl.

8. The anti-allergic composition according to claim 7 wherein n=2.

9. The anti-allergic composition according to claim 7 wherein n=0.

10. The anti-allergic composition according to claim 7 wherein R represents hydrogen, $R^1$ represents $C_{1-6}$alkyl substituted with one $Ar^1$, and B represents NH or $CH_2$.

11. The anti-allergic composition according to claim 10 wherein B represents NH.

12. The anti-allergic composition of claim 7 wherein the compound is a member selected from the group consisting of:
1-ethyl-4-[2-[hexahydro-4-[[3-[(5-methyl-2-furanyl)-methyl]-3H-imidazo[4,5-b]pyridin-2-yl]amino]-1H-azepin-1-yl]ethyl]-1,4-dihydro-5H-tetrazol-5-one;
1-[(4-fluorophenyl)methyl]-N-[hexahydro-1-[2-(pyrimidinylamino)ethyl]-1H-azepin-4-yl]-1H-benzimidazol-2-amine;
1-[(4-fluorophenyl)methyl]-N-[1-[2-(2-pyrimidinylamino)ethyl]-3-pyrrolidinyl]-1H-benzimidazol-2-amine;
1-[(4-fluorophenyl)methyl]-N-[1-[2-(2-thiazolylamino)ethyl]-3-pyrrolidinyl]-1H-benzimidazol-2-amine; and
1-[(4-fluorophenyl)methyl]-N-[1-[2-(2-pyridinyl)ethyl]-3-pyrrolidinyl]-1H-benzimidazol-2-amine.

13. A method of treating allergic diseases in warm blooded animals suffering from the same, which method comprises the systemic administration to warm blooded animals of an effective anti-allergic amount of the anti-allergic composition of claim 7.

14. The method of treating allergic diseases in warm blooded animals suffering from the same, which method comprises the systemic administration to said warm blooded animals of an effective anti-allergic amount of the anti-allergic composition of claim 8.

15. The method of treating allergic diseases in warm blooded animals suffering from the same, which method comprises the systemic administration to said warm blooded animals of an effective anti-allergic amount of the anti-allergic composition of claim 9.

16. The method of treating allergic diseases in warm blooded animals suffering from the same, which method comprises the systemic administration to said warm blooded animals of an effective anti-allergic amount of the anti-allergic composition of claim 10.

17. The method of treating allergic diseases in warm blooded animals suffering from the same, which method comprises the systemic administration to said warm blooded animals of an effective anti-allergic amount of the anti-allergic composition of claim 11.

18. The method of treating allergic diseases in warm blooded animals suffering from the same, which method comprises the systemic adminstration to said warm blooded animals of an effective anti-allergic amount of the anti-allergic composition of claim 12.

* * * * *